US009625884B1

United States Patent
Ousley et al.

(10) Patent No.: US 9,625,884 B1
(45) Date of Patent: Apr. 18, 2017

(54) APPARATUS FOR EXTENDING CONTROL AND METHODS THEREOF

(71) Applicants: Timothy Harris Ousley, Austin, TX (US); Daniel Hawley Ousley, Austin, TX (US)

(72) Inventors: Timothy Harris Ousley, Austin, TX (US); Daniel Hawley Ousley, Austin, TX (US)

(\*) Notice: Subject to any disclaimer, the term of this patent is extended or adjusted under 35 U.S.C. 154(b) by 162 days.

(21) Appl. No.: 14/253,866

(22) Filed: Apr. 16, 2014

Related U.S. Application Data

(60) Provisional application No. 61/832,977, filed on Jun. 10, 2013.

(51) Int. Cl.
*G05B 13/02* (2006.01)
*G09B 21/00* (2006.01)

(52) U.S. Cl.
CPC ......... *G05B 13/0205* (2013.01); *G09B 21/00* (2013.01)

(58) Field of Classification Search
CPC . C12C 1/6837; C12C 2525/15; C12C 1/6895; C12C 2600/158; A61G 7/018; G06F 19/327; G06F 19/3406; G06F 19/3418; G06F 2203/0331; G06F 2203/04808; G06F 3/033; G06F 3/0416; G06F 3/045
See application file for complete search history.

(56) References Cited

U.S. PATENT DOCUMENTS

| | | |
|---|---|---|
| 3,911,316 A | 10/1975 | Feick et al. |
| 3,993,154 A | 11/1976 | Simmons et al. |
| 4,158,196 A | 6/1979 | Crawford, Jr. |
| 4,161,726 A * | 7/1979 | Burson ................ G05G 9/047 200/6 A |
| 4,298,863 A | 11/1981 | Natitus et al. |
| 4,680,790 A | 7/1987 | Packard et al. |
| 4,843,386 A | 6/1989 | Wolf |

(Continued)

FOREIGN PATENT DOCUMENTS

| | | |
|---|---|---|
| CA | 2478421 C | 9/2003 |
| DE | 3418053 A1 | 11/1984 |

(Continued)

OTHER PUBLICATIONS

Able Data. Big Button Electric Bed Control. pp. 1-3. Updated on Sep. 30, 2010. Falls Church, VA. Accessed Apr. 25, 2014 at http://www.abledata.com/abledata.cfm? pageid=19327&top=11412 &ksectionid=19327&productid=83049&trail=0&discontinued=0.

(Continued)

*Primary Examiner* — Quan-Zhen Wang
*Assistant Examiner* — Chico A Fox
(74) *Attorney, Agent, or Firm* — Timothy Daniel Snowden

(57) ABSTRACT

An adjustably adapted control apparatus for facilitating control of controlled apparatus 109 by users who have limited means of physical input for activating currently available control means. Transducing apparatus 102-106 transduces a physical contact input 101 of a user with input limitations, decision making apparatus 107 determines the intended commands of the user based on adjustable adaptation parameters, and directs control signals 109 from signal generator 108 through transmittance apparatus 108, causing the controlled apparatus to effect the intended commands of the user.

14 Claims, 11 Drawing Sheets

(56) References Cited

U.S. PATENT DOCUMENTS

| | | | |
|---|---|---|---|
| 4,979,094 A | 12/1990 | Gemmell et al. | |
| 5,012,165 A | 4/1991 | Lautzenhiser et al. | |
| 5,033,000 A | 7/1991 | Littlejohn et al. | |
| 5,345,226 A | 9/1994 | Rice, Jr. et al. | |
| 5,460,186 A | 10/1995 | Buchhold | |
| 5,542,138 A | 8/1996 | Williams et al. | |
| 5,635,807 A | 6/1997 | Lautzenhiser | |
| 5,764,164 A * | 6/1998 | Cartabiano | A63F 13/06 273/148 B |
| 5,850,212 A * | 12/1998 | Nishibori | G06F 3/04892 340/4.1 |
| 6,008,598 A | 12/1999 | Luff et al. | |
| 6,073,036 A * | 6/2000 | Heikkinen | G06F 3/04842 379/354 |
| 6,222,524 B1 | 4/2001 | Salem et al. | |
| 6,426,600 B1 | 7/2002 | Lautzenhiser et al. | |
| 6,636,763 B1 | 10/2003 | Junker et al. | |
| 6,664,947 B1 * | 12/2003 | Vinogradov | G06F 3/03543 345/157 |
| 6,850,224 B2 * | 2/2005 | Baughman | G06F 3/03543 345/156 |
| 7,071,844 B1 * | 7/2006 | Moise | G06F 3/03547 340/4.11 |
| 7,080,710 B2 | 7/2006 | Kwon et al. | |
| 7,176,898 B2 | 2/2007 | Litwiller | |
| 7,357,202 B2 | 4/2008 | Kamen et al. | |
| 7,535,401 B2 | 5/2009 | Tolmei | |
| 7,541,965 B2 | 6/2009 | Ouchi et al. | |
| 7,779,493 B2 | 8/2010 | Lemire et al. | |
| 7,839,383 B2 * | 11/2010 | Li | G06F 3/014 345/156 |
| 8,006,332 B2 * | 8/2011 | Lemire | A61G 7/005 5/600 |
| 8,018,320 B2 | 9/2011 | Najanguaq Sovso Andreasen Struijk | |
| 8,044,766 B2 | 10/2011 | Ghovanloo et al. | |
| 8,125,448 B2 * | 2/2012 | Ranta | G06F 3/0346 345/157 |
| 8,151,387 B2 | 4/2012 | Osborne et al. | |
| 8,242,880 B2 | 8/2012 | Ghovanloo et al. | |
| 8,258,917 B2 * | 9/2012 | Cai | G06F 3/0346 180/167 |
| 8,432,367 B2 | 4/2013 | Li et al. | |
| 8,441,356 B1 * | 5/2013 | Tedesco | G08B 21/0453 340/539.15 |
| 8,474,794 B2 * | 7/2013 | Liljedahl | A61G 7/1017 254/120 |
| 8,482,525 B2 * | 7/2013 | Moore | G06F 3/0346 345/163 |
| 8,502,641 B2 | 8/2013 | Lautzenhiser | |
| 8,516,561 B2 * | 8/2013 | White | G06F 3/017 726/18 |
| 8,560,004 B1 | 10/2013 | Tsvetkov et al. | |
| 8,570,273 B1 | 10/2013 | Smith | |
| 8,581,845 B2 | 11/2013 | Nikfarjam et al. | |
| 8,681,101 B1 * | 3/2014 | Haney | G06F 3/033 345/161 |
| 8,701,229 B2 * | 4/2014 | Lemire | A61G 7/005 5/510 |
| 8,708,825 B2 * | 4/2014 | Crisco, III | A63F 13/06 463/37 |
| 8,730,159 B2 * | 5/2014 | Norieda | G06F 3/011 345/157 |
| 8,774,878 B2 * | 7/2014 | Amiri | G06F 1/1615 379/433.01 |
| 8,935,637 B2 * | 1/2015 | Kim | G06F 1/1626 345/156 |
| 8,972,030 B2 * | 3/2015 | Cavarec | G08C 17/02 700/17 |
| 9,239,837 B2 * | 1/2016 | Chardon | G06F 17/30011 |
| 9,261,983 B2 * | 2/2016 | Bailen | G06F 3/0317 |
| 2001/0048291 A1 | 12/2001 | Lautzenhiser et al. | |
| 2003/0027107 A1 * | 2/2003 | Fukui | G05B 19/00 434/100 |
| 2003/0076238 A1 | 4/2003 | Moster et al. | |
| 2004/0012559 A1 * | 1/2004 | Seki | G06F 3/0346 345/156 |
| 2004/0207542 A1 * | 10/2004 | Chang | G06F 3/016 341/20 |
| 2005/0007258 A1 * | 1/2005 | Moster | A47C 31/008 340/4.12 |
| 2005/0219210 A1 * | 10/2005 | Leland | G06F 3/038 345/157 |
| 2006/0138989 A1 * | 6/2006 | Yuasa | G05B 19/427 318/568.13 |
| 2006/0227030 A1 * | 10/2006 | Clifford | G08C 17/00 341/176 |
| 2007/0021153 A1 * | 1/2007 | Novak | A61G 12/00 455/566 |
| 2007/0060445 A1 * | 3/2007 | Reinkensmeyer | A61H 1/0274 482/1 |
| 2007/0123227 A1 * | 5/2007 | Hong | G06F 3/03542 455/414.1 |
| 2007/0130692 A1 | 6/2007 | Lemire et al. | |
| 2008/0083141 A1 * | 4/2008 | Treuthardt | E01H 5/00 37/196 |
| 2008/0235872 A1 * | 10/2008 | Newkirk | A61G 7/018 5/600 |
| 2009/0212979 A1 * | 8/2009 | Catchings | G06F 3/014 341/20 |
| 2010/0063822 A1 * | 3/2010 | O'Brien | H04M 1/72588 704/271 |
| 2010/0151916 A1 | 6/2010 | Baek et al. | |
| 2010/0231547 A1 | 9/2010 | Pryor | |
| 2010/0308999 A1 * | 12/2010 | Chornenky | G08B 6/00 340/573.1 |
| 2010/0321214 A1 * | 12/2010 | Wang | G06F 3/0416 341/20 |
| 2011/0019370 A1 * | 1/2011 | Koh | H01L 21/561 361/749 |
| 2011/0063073 A1 | 3/2011 | Su et al. | |
| 2011/0069024 A1 * | 3/2011 | Kim | G06F 3/01 345/173 |
| 2011/0143898 A1 * | 6/2011 | Trees | A61G 7/005 482/142 |
| 2011/0199298 A1 * | 8/2011 | Bassompiere | G01C 21/16 345/157 |
| 2011/0304648 A1 * | 12/2011 | Kim | G06F 1/1626 345/633 |
| 2012/0185090 A1 | 7/2012 | Sanchez et al. | |
| 2012/0215360 A1 * | 8/2012 | Zerhusen | A61G 7/018 700/275 |
| 2012/0253483 A1 * | 10/2012 | Cavarec | G08C 17/02 700/83 |
| 2013/0069886 A1 * | 3/2013 | Wang | G06F 3/044 345/173 |
| 2013/0234826 A1 | 9/2013 | Sekiguchi et al. | |
| 2013/0306120 A1 * | 11/2013 | Fukunaga | A61H 3/04 135/66 |
| 2013/0318716 A1 | 12/2013 | Vanderpohl, III | |
| 2014/0039351 A1 | 2/2014 | Mix et al. | |
| 2014/0062867 A1 | 3/2014 | Baumgartner | |
| 2014/0267054 A1 * | 9/2014 | Moore | G06F 1/169 345/168 |
| 2015/0066275 A1 * | 3/2015 | Masaki | B62B 5/0073 701/22 |
| 2015/0129741 A1 * | 5/2015 | Okuda | A61B 19/28 248/550 |
| 2015/0231006 A1 * | 8/2015 | Bhimavarapu | A61G 7/018 5/621 |

FOREIGN PATENT DOCUMENTS

| | | |
|---|---|---|
| EP | 0123430 A1 | 10/1984 |
| EP | 0525301 A1 | 2/1993 |
| EP | 1107207 A2 | 6/2001 |
| EP | 2570897 A2 | 3/2013 |
| GB | 956302 A | 4/1964 |

(56) References Cited

FOREIGN PATENT DOCUMENTS

| WO | 9307726 | A1 | 4/1993 |
|----|---------|----|--------|
| WO | 0118781 | A1 | 3/2001 |
| WO | 2011055326 | A1 | 5/2011 |
| WO | 2012059601 | A1 | 5/2012 |
| WO | 2012099686 | A2 | 7/2012 |
| WO | 2013101220 | A1 | 7/2013 |

OTHER PUBLICATIONS

AbleData. Cursor Control Interface. pp. 1-9. nd. AbleData, Falls Church, VA. Accessed May 13, 2014 at http://www.abledata.com/abledata.cfm?pageid=19327&ksectionid=19327&top=11144.

AbleData. Television Remote Control. pp. 1-5. nd. AbleData, Falls Church, VA. Accessed May 11, 2014 at http://abledata.com/abledata.cfm?pageid=19327&ksectionid=19327&top=12747.

AbleData. TV Controller 2. p. 1. nd. AbleData, Falls Church, VA. Accessed May 11, 2014 at http://abledata.com/abledata.cfm?pageid=19327&top=12747&ksectionid=19327&productid=194778&trail=0&discontinued=0.

AbleNet, Inc. Introduction to the Imperium® 200H. pp. 1-29. Roseville, MN. Mar. 2005. Accessed Apr. 25, 2014 at http://store.ablenetinc.com/downloads/manuals/Imperium_200H_User_Manual.pdf.

Agyei-Ntim, Frank, et al. "System Configuration and Simulated User Evaluation of enRICH." The Second International Symposium on Quality of Life Technology. Jun. 28-Jun. 29, 2010, Las Vegas, NV. University of Pittsburgh, Pittsburgh, PA. Accessed May 13, 2014 at https://sites.google.com/site/biothemonitors/publications/Ntim%202010.pdf.

Assistive Technology Solutions. Advanced Technology for Greater Independence. pp. 1-3. 2014. Assistive Technology Solutions LLC, Franklin, TN. Accessed May 12, 2014 at http://www.atsaac.com/ancillary-products/.

Centre for Excellence in Universal Design. Keypads. pp. 1-7. 2014. National Disability Authority, Ballsbridge, Dublin, Ireland. Accessed May 13, 2014 at http://www.universaldesign.ie/useandapply/ict/itaccessibilityguidelines/smartcards/guidelines/smartcardguidelines/keypads.

Crest Healthcare Supply. HD2™ Bed Controls. pp. 1-3. 2010. Crest Healthcare Supply, Dassel, MN. Accessed May 13, 2014 at http://www.cresthealthcare.com/HD2%E2%84%A2-Bed-Controls_266.

Curbell Inc. Curbell Medical Nurse Call and Television Products. pp. 1-76. 2012. Curbell, Inc., Orchard Park, NY. Accessed Apr. 1, 2014 at http://www.curbellmedical.com/files/pdf/MAP466C_nurse_call_catalog.pdf.

GimpGear Design & Mfg. Ultimate Arcade 2 Limited Dexterity Video Game Controller. pp. 1-4. 2011. Broadened Horizons Inc., Maple Grove, MN. Accessed May 13, 2014 at http://www.gimpgear.us/ultimate-arcade2.

Gober, George. Home Automation Overview. pp. 1-30. nd. AssistTech.info. Accessed May 12, 2014 at http://assisttech.info/resources/presentations/home_automation.pdf.

Goldman, Matthew, et al. "Remotely Controlled Communication and Control System for Limited Mobility Individuals." IEEE 13th International Conference on e-Health Networking, Applications and Services. Jun. 13-Jun. 15, 2011, Columbia, MO. pp. 90-93. IEEE, New York, NY. Accessed May 13, 2014 at https://sites.google.com/site/biothemonitors/publications/Goldman2011.pdf.

Hill-Rom. Advanta™ 2 Med Surg Bed. pp. 1-2. 2014. Hill-Rom, Batesville, IN. Accessed May 13, 2014 at http://www.hill-rom.com/usa/Products/Category/Hospital-Beds/Advanta-2-med-surg-bed/.

Hill-Rom. Hill-Rom® 1000 Medical Surgical Bed. pp. 1-2. 2014. Hill-Rom, Batesville, IN. Accessed May 13, 2014 at http://www.hill-rom.com/usa/Products/Category/Hospital-Beds/Hill-Rom-1000-medical-surgical-bed/.

Hill-Rom. Hill-Rom® 405 Electric Hospital Bed. pp. 1-2. 2014. Hill-Rom, Batesville, IN. Accessed May 13, 2014 at http://www.hill-rom.com/usa/Products/Category/Hospital-Beds/Hill-Rom-405-electric-hospital-bed/.

Hill-Rom. Hill-Rom® Resident® Long Term Care Bed. pp. 1-2. 2014. Hill-Rom, Batesville, IN. Accessed May 13, 2014 at http://www.hill-rom.com/usa/Products/Category/Hospital-Beds/Hill-Rom-Resident-Long-Term-Care-Bed/.

Hill-Rom. TotalCare® Connect bed. pp. 1-2, 2013. Hill-Rom Australia, Auburn NSW, Australia. Accessed May 13, 2014 at http://www2.hill-rom.com/medicraft/TotalCare_Connect.htm.

Huang, Yirui and Kimberly Newman. "Improved Quality of Care with Remote Activity and Fall Detection Using Ultrasonic Sensors." 34th Annual International Conference of the IEEE EMBS. Aug. 28-Sep. 1, 2012, San Diego, California. pp. 5857-5857. IEEE, New York, NY. Accessed May 13, 2014 at https://sites.google.com/site/biothemonitors/publications/17591115.pdf.

Jacobson, Julie. Home Automation Brings Dignity, Independence to Residents with ALS. CEPro.com. pp. 1-3. Oct. 18, 2013. EH Publishing, Inc, Framingham, MA. Accessed May 13, 2014 at http://www.alsri.org/uploads/8/5/0/2/8502739/111018-home_automation_brings_dignity_independence_to_residents_with_als_-_ce_pro.pdf.

Jeary, Tom. The TV Controller 2. pp. 1-2. nd. Workshop Solutions. Accessed May 12, 2014 at http://www.workshopsolutions.com/COMPLETE/tvcon2.htm.

Marsden, Randy. NEMO: Speak, Control, Relax. pp. 1-8. 2000. Technology and Persons With Disabilities Conference 2000. California State University Northridge Center on Disabilities, Northridge, CA. Accessed May 12, 2014 at http://www.csun.edu/cod/conf/2000/proceedings/0186Marsden.htm.

Montana State University. Wireless Hospital Bed Controller: A Better Way of Interfacing: Ezra II System. 2012. pp. 1-12. Bozeman, MT. Accessed Apr. 24, 2014 at http://www.coe.montana.edu/ee/seniordesign/archive/FL12/WirelessContrHospitalBed/mysite.php?page=1.

Newman, Kimberly. Current BIO Projects. pp. 1-2. nd. University of Colorado Boulder, Boulder, CO. Accessed May 12, 2014 at http://www.colorado.edu/ECE/biothemonitors/projects.html.

Newman, Kimberly. Smart Hospital Room for Individuals with Limited Mobility. pp. 1-16. nd. United States Food and Drug Administration Functional Performance and Device Use Laboratory, Silver Spring, MD. Accessed May 12, 2014 at http://ecee.colorado.edu/news/seminar_slides/slides2012/2012F_Newman.ppt.

Newman, Kimberly. Smart Hospital Room. pp. 1-6. nd. University of Colorado Boulder, Boulder, CO. Accessed May 1, 2014 at http://ecee.colorado.edu/~ecen5623/Smart-Hospital-Room.pdf.

Oklahoma ABLE Tech. Assistive Technology Checklist. pp. 1-13. 2014. The Galvin Group LLC, Tucson, AZ. Accessed May 13, 2014 at http://www.galvin-group.com/media/21436/ATchecklist.doc.

Pandaboard.org. EZRA II Environment Control System. nd. p. 1. Pandaboard.org. Accessed Apr. 24, 2014 at http://pandaboard.org/content/ezra-ii-environment-control-system.

Possum Ltd. Possum Product Catalogue. pp. 1-35. nd. Possum Ltd, Aylesbury, Bucks, UK Accessed Apr. 1, 2014 at http://www.possum.co.uk/static/uploads/PossumProductCatalogue.pdt.

Product Design and Development Corp. Replacement Controls for Beds and Lifts. p. 1. 2014. Product Design and Development Corp, St. Louis, MO. Accessed May 13, 2014 at http://www.pddcorp.com/replacement_bed_controls.htm.

Quickie-Wheelchairs.com. Quickie Pulse 6. p. 1. 2014. Southwest Medical, Phoenix, AZ. Accessed May 13, 2014 at http://www.quickie-wheelchairs.com/products/Quickie-Pulse-6-26107.html.

Rauland. Faster Bed Turnover, Better Bed Management. p. 1. 2014. Rauland, Chicago, IL. Accessed May 12, 2014 at http://web.rauland.com/Bed_Managementcfm.

Rauland. Resident Care: Promoting Safety, Preserving Independence, Providing Peace of Mind. p. 1. 2014. Rauland, Chicago, IL. Accessed May 12, 2014 at http://web.rauland.com/Workflow_Resident_Care.cfm.

Rauland. Responder® 5: Delivering Speed and Simplicity in a Complete Nurse Call System. p. 1. 2014. Rauland, Chicago, IL. Accessed May 12, 2014 at http://www.rauland.com/responder5.cfm.

(56) References Cited

OTHER PUBLICATIONS

RehabMart, LLC. Communication Aids. pp. 1-7. 2014. RehabMart, LLC, Elberton, GA. Accessed May 13, 2014 at http://www.rehabmart.com/category/Communication_Aids.htm.

Shah, Niket, Maulik Kapuna, and Kimberly Newman. "Embedded Activity Monitoring Methods," Activity Recognition in Pervasive Intelligent Environments, pp. 291-311. 2011. Atlantis Press, Amsterdam, Beijing, & Paris. Accessed May 13, 2014 at https://sites.google.com/site/biothemonitors/publications/Chapter13EmbeddedActivityMonitoringMethods.pdf.

University of Birmingham NIHR Horizon Scanning Centre. Tongue Drive Interface System for People with Severe Disability, Technology Alert. pp. 1-2. Sep. 2013. Edgbaston, Birmingham, UK. Accessed Mar. 19, 2014 at http://www.hsc.nihr.ac.uk/files/downloads/2144/2462.4ae4dce5.GTBionicsLabTonqueDriveSystemfinal.pdf.

* cited by examiner

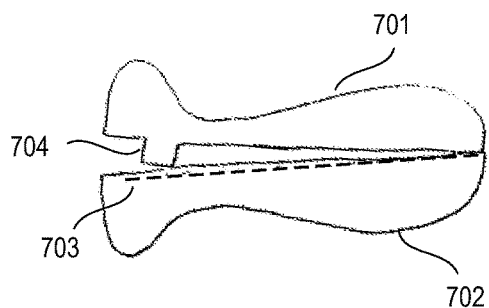
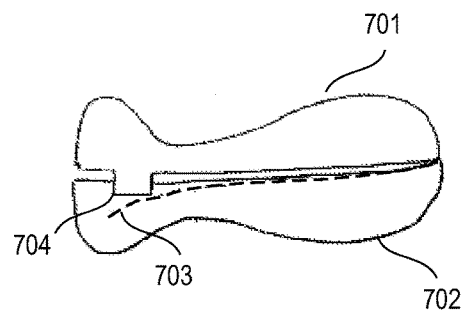
FIG. 7A    FIG. 7B
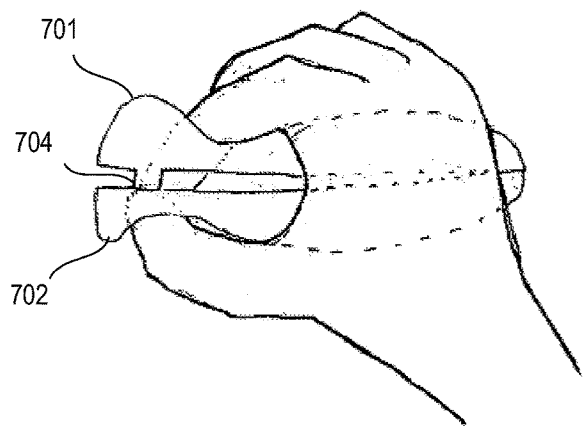
FIG. 7C

APPARATUS FOR EXTENDING CONTROL AND METHODS THEREOF

CROSS-REFERENCE TO RELATED APPLICATION

This is a non-provisional utility application claiming the priority of the U.S. provisional patent application No. 61/832,977 filed 10 Jun. 2013, which is herein incorporated by reference.

FEDERALLY SPONSORED RESEARCH

Not Applicable

SEQUENCE LISTING

Not Applicable

BACKGROUND OF THE INVENTION

Many people are living with seriously debilitating diseases. While medicine can serve as a means to prolonging a patient's life, many patients still have significant difficulty in interacting with and functioning in their environments. The goal of medical therapies and technologies is to enable the patient to interact with their environment as much as possible for as long as possible—in other words, to adapt a patient's limited abilities to still function as normally as possible. This benefits patients and caregivers alike, as the patient continues to be as productive and interactive as possible while relying as little as possible on caregiver resources.

In particular, many patients suffer from reduced muscle function or control. Underlying causes include diseases of the muscle, such as myopathies, dermatomyositis, polymyositis, and muscular dystrophy, and diseases of the nervous system, such as amyotrophic lateral sclerosis (ALS, often known as Lou Gherig's disease, and often accompanied by severe speech impairment), Bell's palsy, botulism, Guillain-Barre syndrome, myasthenia gravis, neuropathy, poisoning, polio, stroke, injury, paralysis, and Parkinson's disease (and other motor system disorders). Those afflicted with these diseases lose, or never had, the capability which most people are blessed with of interacting with and directing their environment. As an example, some patients may not have strength to move their body to a comfortable position in bed, a particular problem for those who are confined to bed for extended or indefinite periods, and must somehow shift their weight to avoid bed sores. For such patients, motorized electric hospital beds have been developed with controllers, such as remote control pendants, intended to allow the patient and caregiver to easily adjust the bed. These controllers are typically equipped with many buttons that patients or caregivers can press to actuate various bed motors that control such functions as raising and lowering the head or feet, tilting the bed, and moving the bed, among other settings.

In not a few cases, the patient may lack the ability to manipulate buttons, even large ones, or may not possess the dexterity to move between the multiple buttons and controls necessary to direct the various functions. In these cases, the controller is then typically used by the caregiver—when a caregiver is even present—who must guess the settings needed to make the patient comfortable. This is a slow, frustrating process for both patient and caregiver, especially if a patient cannot verbally communicate, and made even more so when adjustments are required in the middle of the night.

Field of the Invention

This invention relates to electronically communicating one or more users' intended commands. In particular, it is directed towards at least partially enabling handicapped persons to communicate their commands to one or more devices.

Description of the Related Art

The long felt need for enabling handicapped people to interact more with their environment has led to the creation of a number of tools and devices. Current standard input technologies include push buttons, switches, remote controls, and knobs. Examples of other control means for disabled persons include sip-and-puff switches, eye-tracking systems, voice control systems, joysticks, touch screens, head control systems, and tongue control systems. Such systems may be less than desirable for reasons including: difficulty to operate, tediousness, inability to operate, obtrusiveness, and unsightliness.

Many simple controls have been adapted to use by persons with various handicaps by superficial changes in geometry and surfaces. Larger knobs and color-coded buttons, for example, are obvious changes intended to provide a measure of assistance. These alterations, however, are often inadequate: larger knobs are of little use if a user cannot even turn a knob, and color-coded buttons avail nothing if one's hand is shaking badly.

Input methods intended to more directly address user needs include familiar technologies such as sip-and-puff (SNP) switches, which can be problematic during sleep and for those with sleep apnea or breathing troubles, where a positive air pressure system or ventilation system may interfere with operation of the SNP device. Multi-level and multi-input switches such as joysticks, potentiometer-based switches, and variable output switches seek to offer more fine-grained and versatile control via one (or at least fewer) input methods, but can present nearly insurmountable challenges to many patients, such as those with loss of fine motor movement or significant tremors. Similarly, tilt switches require ability to tilt some part of body to a measurable and repeatable degree and are prohibitively restrictive for individuals with extreme impairments. Additionally many assistive switch-based interfaces are designed only for use with one particular device, a wheelchair being a very common example.

Various interfaces are available which employ some form of touch or grip-based inputs, both digital and analog. While these can often be very intuitive for a fully functioning user, they typically only offer calibration adjustments, but no ability to adjust the activation parameters to a particular user's capabilities, and thereby requiring a very precise level of control to consistently and accurately activate the desired commands. In addition, such devices are typically not configured to remap existing control inputs in order to serve as a user-customized controller without significant hardware and/or software changes. Further, many are specifically limited to mobile or computing devices, with practically no options for extending the control means to other devices and functions.

Yet other controllers seek to provide a means of remapping a standard control interface to a more advantageous interface for able persons with specific needs or disabled persons with specific handicaps. Such systems include tongue-based control, eye-tracking technology, finger-worn keyboard and/or mouse replacements (or other similar bodywearable devices), and shoulder switches. Various entities are actively exploring tongue-based control for people with limited muscle strength and control, but the technology faces inherent drawbacks in its cumbersomeness to use and its obvious failure for those with tongue paralysis or impairment from conditions such as bulbar palsy or ALS. Further, some tongue controllers require a permanent or semi-permanent magnet or other object in the user's mouth, which may be uncomfortable or dangerous, particularly when sleeping or undergoing certain imaging procedures, such as MRI. Although many people have found eye tracking helpful, it requires considerable complexity and cost to implement, and is subject to additional environmental factors limiting its performance, such as flickering lights or shadows, requirements for minimum brightness levels to properly function, tired eyes, or movement of the eye tracking system. Currently known shoulder switches are limited by the dexterity and strength required of the shoulders, difficulty in body positioning and posture, and a maximum of one output for every means of input, thereby limiting the system to two control outputs.

Other devices include input extending controllers that seek to offer a universal replacement for multiple control interfaces. Such devices include combination keyboard and mouse replacements such as finger mounted unified input methods, controllers of multiple devices including property management controllers, nurses' station controllers, and universal remote controls. These devices often require considerable dexterity, are very slow to operate, and provide no assistance unless the person is able to operate at least one of a very restrictive set of possible controls. Further, many of these devices are restricted to use only in conjunction with a particular device (e.g. a wheelchair control that also offers a nurse's bell or television controller), and so have limited application.

State-based controllers and controllers with a hierarchy of available control options that are cyclically presented for actuation by a single control set are offered for both able people as well as for persons with various types and degrees of disabilities. Regrettably, these systems are often 'scanning style' or window-of-opportunity based, requiring very specific timing of inputs, rendering them ineffective for people with severe disabilities that negatively impact their abilities to meet the timing requirements; are not ergonomic; are often slow to operate, especially when controlled only by one switch; and have limited input options (such as regular switches and knobs or SNP switches) that require considerably dexterity and thereby render the system unusable by those with severe dexterity loss. Many such interfaces are also expensive due to the displays employed.

Further, many control means rely on digital transducers with one bit of resolution, typically making the interface unadaptable to the needs of the user. This lack of adjustability frequently renders the device of limited to no utility for people with severe impairments. Still other devices seek to rectify perceived deficiencies in control means by accepting analog inputs and providing analog signals out (such as joysticks for wheelchair controls); however, analog outputs are largely inadequate as control signals for most device functions, which often require binary, on/off, yes/no type inputs. Thus, these types of control means are unable to remap most standard control means. Finally, other control means fail to provide any form of feedback to the user, which may often limit the user's ability to know what will happen when a given input means is activated, thereby leading to non-usage, or to uncomfortable, embarrassing, or dangerous situations.

As the computer and mobile device industries continue to develop new variations, and the phone and tablet industries in particular proliferate, an increasing number of software solutions are offered for use by able and disabled persons to extend control over their environment from a familiar user interface—monitoring heart rate, controlling insulin pumps, opening a garage door, ordering pizza, and remotely controlling a 3D printer with an iPhone are only a few examples. However entertaining and convenient these functions may be, they are inherently limited by the hardware interface required to interact with the software. A person lacking significant fine motor control, for example, will likely find little value in an iPhone based interface for controlling all the devices surrounding him; however close to his fingers the means for actuation may be sitting.

Clearly, an improved means is needed for remapping and/or relocating functions from standard, complex control interfaces to a control means adapted to the particular needs of the user, and capable of utilizing for control of those functions the limited range of physical inputs the user is able to reliably control.

BRIEF SUMMARY OF THE INVENTION

Disclosed herein are apparatus and methods for facilitating control of apparatus by persons who are unwilling to, unable to, or have difficulty in activating currently available control means. Control available to persons with decreased means of physical input is thereby extended by providing a control apparatus that may be adjusted to accept the user's physical control inputs, and consequently output signals sufficient to control standard devices or systems consistent with the intended purpose of the user, thereby effectively remapping the control means of the controlled device(s) to a control means more suitable for the user(s) particular situation. The control apparatus is at least partially configured to be physically integrated into one or more of said controlled apparatus, or physically independent from all of said controlled apparatus, or any combination thereof.

In one embodiment of the invention, the user is able to cycle through available states. In a further embodiment, this cycling is performed upon repetitive commands that each advance the controller by one state. Other embodiments may advance through any predetermined number of states before stopping, may advance until a stop command is given, may advance through all available states before stopping, as well as other possibilities that will readily present themselves to persons skilled in the art.

In one embodiment, the user is able to activate the current state by giving an activation command(s), which may be identical, similar to, or separate from the state-advancing command(s). In yet other embodiments, a state that is currently activated may be deactivated by completion of the action initiated by the current state, by initiation of a sustainable action initiated by the current state, by the user ceasing to give the activation command, by the user giving a deactivation command, by a combination of these options, or by other readily discernible possibilities.

In one embodiment, the transducing means is at least partially contained in one or more housings suitable for gripping in a human hand. In a further embodiment, the user holds in each hand a single unit configured to sense the user's grip. These two grip units measure the amount of grip from the user and can be adjusted to match the user's strength. Each pendant is actuated when the user applies an adjustably predetermined grip intensity, which may be the same or different between the two pendants. One pendant is used by the user to change the current state of the control apparatus's decision making means, while the other is used to activate and deactivate the new current state by squeezing the grip unit with appropriate intensity to activate the selected state and releasing (or loosening the hold on) the grip unit to deactivate it. Alternatively, the second grip unit could be squeezed once to activate the current state, released, and squeezed again to deactivate it, to eliminate the need for the user to maintain a constant grip intensity. A combination of approaches may also be employed. Similarly, the first pendant may be configured to allow the user to continue to squeeze the grip unit to advance through the states, without having to release or loosen the hold on it, or a combination of those methods.

In another embodiment, the housing(s) are at least partially chosen to be fitted somewhat specifically to one or more users so that the users may more advantageously activate the controller.

In another embodiment, a preferred geometry or geometries for the housing(s) are chosen by one or a combination of methods for selecting a preferred shape for fitting the body portion of the user(s).

In another embodiment the user's physical contact inputs are transduced by one or more fingertip-actuated buttons.

In another embodiment the control apparatus provides the user with feedback to confirm commands, convey information about the current state, convey information regarding the predicted result of one or more inputs, any combination of these, or other readily discernible possibilities.

In various embodiments, the control apparatus monitors controlled apparatus and optionally provides feedback on status of the monitored apparatus, stores and accesses stored parameters for multiple users, or employs machine learning techniques.

In various embodiments, the control apparatus is configured to control at least one apparatus that is a personal support device (such as a hospital bed or chair), alarm or request for help, media device (such as television, radio, disc player, or MP3 player), computing device (such as a personal computer or tablet computer), communication device (such as a communication aid, a text-to-speech device, phone, or smartphone, or a mobility device (such as a wheelchair).

BRIEF DESCRIPTION OF THE SEVERAL VIEWS OF THE DRAWINGS

FIG. 7A, FIG. 7B, and FIG. 7C are illustrations of operation of one portion of the transducing apparatus in a grip-sensing embodiment.

DETAILED DESCRIPTION

Figure 1:
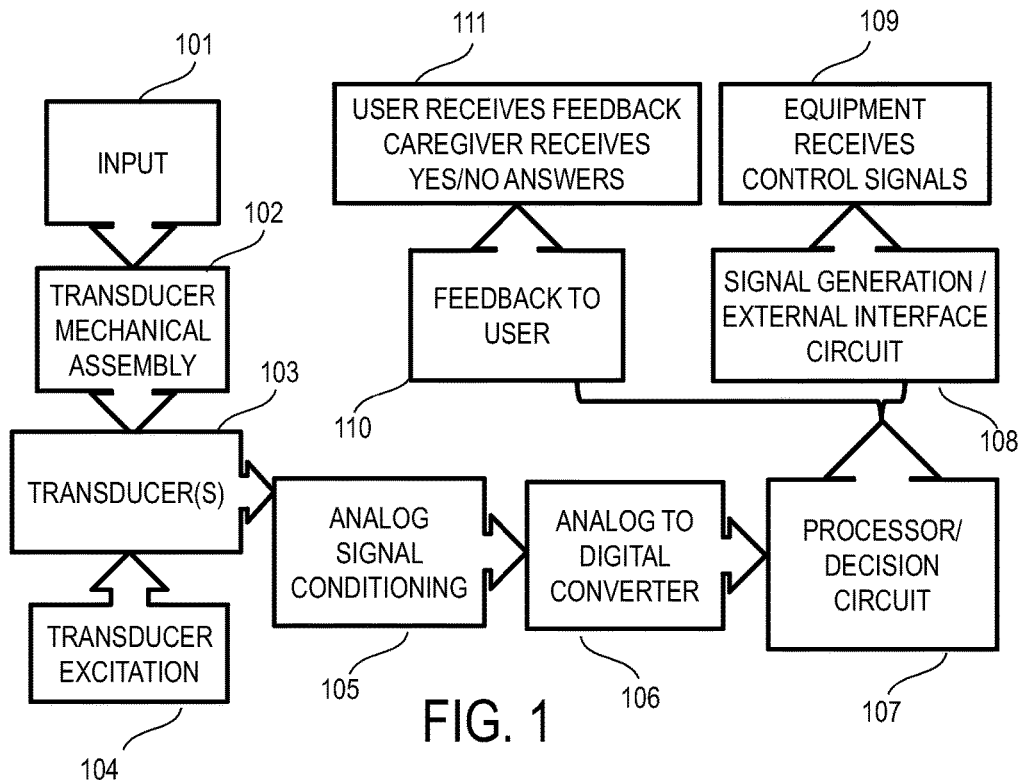
FIG. 1 is a generalized block diagram of selected components of a general embodiment.
Figure 2:
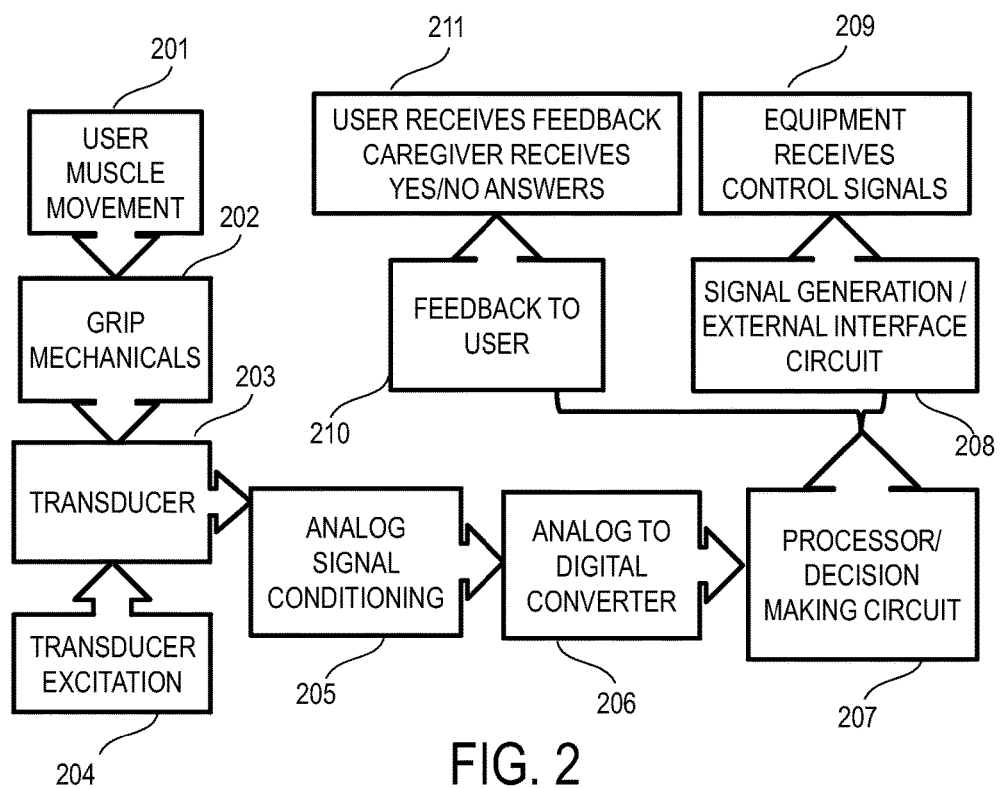
FIG. 2 is a generalized block diagram of selected components of a grip-sensing embodiment.

The following description of various embodiments of the invention, combined with the associated drawings, enables persons of ordinary skill in the art to both practice the preferred embodiments of the invention, and to understand related applications and embodiments of the invention that may not be specifically set forth, but are encompassed by the specification and claims.

GENERAL EMBODIMENT

Embodiments disclosed herein relate to control apparatus and methods for persons desirous of using a limited range of physical contact inputs to effect commands directed to one or more controlled apparatus. In a general embodiment, the control apparatus is comprised at least of a transducing apparatus, a decision making apparatus, at least one signal generator, and a transmittance apparatus, and provides key adjustability and processing methods for deciphering an intended actuation by a user.

The transducing apparatus contains one or more transducers configured to transduce one or more physical contact inputs, which are applied to said transducing apparatus by one or more users, and which, apart from the control apparatus, are inadequate to control one or more functions of the controlled apparatus. At least some of the physical contact inputs are those inputs of insufficient variety, of insufficient intensity, of insufficient distinctness, or of a different nature of input than those inputs required to activate at least one existing control means of any one or combination of the controlled apparatus.

While the primary means for the user to effect his or her intended commands will be through the physical contact inputs just described, this in no way limits the possibility of employing other inputs for auxiliary or supplemental commands or configuration purposes, or of simultaneous deployment or integration of an embodiment of this invention into one or more other devices which employ other types of inputs.

At least one of the transducers in the transducing apparatus is a digital transducer of at least two bits of resolution, an analog sensor, or a magnetically activated digital transducer. The transducing apparatus will generate from the physical contact inputs applied to it one or more electrical signals.

The electrical signals generated by the transducing apparatus in response to physical contact inputs are received by the decision making apparatus. The decision making apparatus determines from these electrical signals what command(s) the user(s) intended by the physical contact input(s) applied, and directs a signal generator to generate one or more resulting control signals sufficient to effect the intended command(s).

The decision making apparatus is capable of determining the intended command(s) of the user(s) due to one or more appropriate parameters configuring the control apparatus. Specifically, these parameters will be mechanical or electrical parameters, or any combination thereof, such parameters configuring either the transducing apparatus or the decision making apparatus or both. Further, any other parameter or combination of parameters may be additionally used.

A single command intended by the user may be represented by a range of different physical contact inputs (e.g. shaky touches, squeezes of varying force, rotations of various angles), which must be interpreted by the decision making apparatus to determine the single command intended thereby. This may be accomplished, as described both above and in specific embodiments and examples following, by configuring the transducing apparatus or the decision making apparatus, or both, such that only one appropriate control signal or set of control signals results from the application of the range of physical contact inputs representing the intended command. The key is that the parameters enable the control apparatus to be adjustably adapted to make the physical contact inputs which the user(s) desires to apply result in effecting the commands which the user(s) intended to give. The appropriate adjustment(s) may be made directly, indirectly, or remotely; may be made by any user or combination of users; may be, as mentioned previously, mechanical or electrical in nature and may affect the transducing apparatus or the decision making apparatus; may be made in part or whole by algorithms; or may be any combination of the adjustment(s) and methods of making them just described.

The decision making apparatus directs one or more signal generators to generate a control signal(s) sufficient to direct the controlled apparatus(es) to effect the intended command(s) of the user(s).

The transmittance apparatus conveys the control signal(s) to the controlled apparatus(es) such that it effects the user(s)' intended command(s).

In various embodiments, the control apparatus may be wholly or partially physically integrated into one or more of the controlled apparatus, may be physically independent from all of the controlled apparatus, or may have elements that are integrated as well as standalone elements that exist independently of the controlled apparatus.

Various embodiments of the control apparatus may be specifically configured for users with various input limitations caused by myopathy (M), dermatomyositis (DM), polymyositis (PM), muscular dystrophy (MD), amyotrophic lateral sclerosis (ALS), palsy (PA), botulism (BO), Guillain-Barre syndrome (GBS), myasthenia gravis (MG), neuropathy (N), poisoning (PI), polio (PL), stroke (S), injury (I), spinal cord injury (SCI), paralysis (P), cerebral palsy (CP), multiple sclerosis (MS), dystrophy, spina bifida (SB), various cardiac disorders (CD), brain injury (BI), repetitive strain injury (RSI), brain tumor (BT), essential tremors (ET), Parkinson's disease (PD), overactive thyroid (OT), absent limb (AL), amputation (AMP), arthritis (A), surgery (SX), or aging (AG). Still other embodiments may be specifically configured for able users who wish to provide a control apparatus configured specifically for their desired input methods for one or more devices they desire to control. Example input limitations and causes are contained in TABLE 1.

Method of Use

To effect a desired command using an embodiment of this invention, a user applies to the transducing apparatus (typically through one or more transducing mechanical apparatus of the transducing apparatus) a physical contact input(s) that appropriately represents the intended command(s). The transducing apparatus generates from the physical contact input an electrical signal(s). This electrical signal is used by the decision making apparatus, in conjunction with an appropriate parameter(s), to determine the command intended by the user, and a control signal(s) appropriate to the controlled apparatus is consequently generated by a signal generator(s) at the direction of the decision making apparatus. This control signal is conveyed to the controlled apparatus by the transmittance apparatus. The controlled apparatus consequently effects the result intended by the user.

Specific examples and embodiments of this method and related apparatus will serve to illustrate to persons skilled in the art the broader concepts disclosed.

DEFINITIONS

Following is a list of specific nomenclature used in reference to the invention disclosed herein and embodiments thereof. This list is provided as an aid to understanding the invention, and should be taken in the context of the full specification. In many cases, further embodiments and specific examples disclosed elsewhere in this document will further clarify the meaning, usage, and scope of a particular term.

(D1) User: As used herein, 'user' refers to any person interacting with any part of the invention to utilize, modify, adjust, install, or position it in any manner. Potential users of the invention include: a patient; a disabled person; or a person with reduced capacity for physical control, physical input, or physical interaction. Potential users further include: an equipment installer; a family member, friend, volunteer, caregiver, or attendant; or any other person involved in the care of a person; as well as able bodied persons wishing to extend control available using a limited set of inputs.

(D2) Physical contact input: For the purposes of this invention, a 'physical contact input' is a user's interaction with one or more transducing apparatus for the eventual purpose of giving one or more commands to the controlled apparatus. Such an interaction is characterized by some portion of the user's body, possibly through a mediating article or apparatus (such as a glove, stylus, clothing, bandage, etc.), coming into contact with one or more transducing apparatus. Examples of physical contact inputs are presented in TABLE 2, and examples of transducers that may be employed in transducing physical contact inputs are included in TABLE 3.

(D3) Input limitation: As used herein, an 'input limitation' is some restriction of the inputs which a user can employ to command a controlled apparatus. Input limitations may be imposed by necessity (such as in the case of a handicapped user) or convenience (such as in the case of an able user), and are somehow inadequate to operate a controlled apparatus absent an appropriate embodiment of this invention. For the purposes of this invention, the input limitations are specifically any one or combination of those listed in TABLE 1, and fall into at least one of the following four classes of limitations which make a specific input employed by a user insufficient to activate at least one of an existing control means of a controlled apparatus:

(i) a different nature than inputs required—the user's available inputs are limited to control inputs of a different nature than the inputs required for the controlled device (ii) insufficient variety—the user has an input limitation because of having insufficient variety of muscle movements required for the controlled device (iii) insufficient intensity—insufficient intensity of muscle action required by the controlled device (iv) insufficient distinctness—muscle action while attempting activation of the controlled device is insufficiently distinct from muscle action while not activating the controlled device, such that activation is either not achieved, or occurs accidentally, or is unreliably achieved.

(D4) Controlled apparatus: As used herein, a 'controlled apparatus' is a device, system, or some other apparatus, at least one function of which may be desirable for one or more users to control using some embodiment(s) of the present invention. Examples include hospital beds, television sets, call alarms, radios, telephones, lighting, doors and locks, automatic doors, and wheelchairs.

(D5) Intended command: As used herein, an 'intended command' is given by a user, and directed toward a controlled apparatus. It is the purpose of the several embodiments of the invention to allow a user to effect intended commands through physical contact inputs which the user's input limitations would otherwise render inadequate for interacting with the existing or typical control means of the controlled apparatus. Examples of intended commands will be obvious upon reading the various examples and embodiments disclosed herein. Such examples include raising or lowering a portion of the hospital bed, opening or closing a motor-actuated door, turning on or off lights, lamps, and other accessories, as well as various commands directed to computing and media devices.

(D6) Analog sensor: As used herein, an 'analog sensor' is a transducer that changes an electrically measureable property (such properties are well known in the art, and examples include voltage, current, resistance, inductance, capacitance, impedance, resonant frequency, filter frequency, gain, and filter strength) with respect to a physical phenomena. Examples of such transducers are included in TABLE 3.

(D7) Digital Transducer: As used herein, a 'digital transducer' is an analog sensor with an integrated digitizing circuit. Examples of such transducers are in TABLE 3. Digital transducers may return data using various methods, examples of which are included in TABLE 4.

(D8) Input signals: As used herein, an 'input signal' in the context of an input to a decision making apparatus is an electrical signal from the transducer to the decision making apparatus. Examples of possible input signals to various decision making apparatus are listed in TABLE 5.

(D9) Transducers: As used herein, a 'transducer' is a structure which converts one or more variations in a physical quantity into an electrical signal. Examples of physical quantities which may be transduced in embodiments of this invention are displayed in TABLE 2. Transducers may be an analog sensor or a digital transducer. For the purposes of this invention, at least one transducer in every embodiment will be:

(i) an analog sensor, (ii) a digital transducer of at least two bits of resolution, or (iii) a magnetically actuated digital transducer, and will be configured to transduce one or more physical contact inputs. Examples of transducers that may be used in various embodiments are in TABLE 3.

A transducer differs from a transducing apparatus in that a transducer refers to a single sensor or digital transducer, while the entire transducing apparatus refers to the totality of the means for generating electrical signals from physical contact inputs, and may include multiple transducers as well as additional structures used to accomplish the transducing apparatus's intended function.

Although at least one input applied to any embodiment must include physical contact for the purposes of this invention, a transducer itself need not be physically contacted by the user, because the transducer may be physically separated from the user input. Regardless, the user must physically contact some portion of the transducing apparatus (typically a transducer mechanical assembly) while applying a physical contact input.

(D10) Transducing apparatus: As used herein, a 'transducing apparatus' is a structure which accepts one or more physical contact inputs and generates one or more resulting electrical signals. The transducing apparatus may be a single transducer or any collection of transducers, signal conditioners, housings, and any other related structures and means necessary or desirable for the intended function of the transducing apparatus.

Examples of transducing apparatus include hand-held pendant-style grips, a system of shoulder switches, and a system of buttons mounted for fingertip activation. Additionally, transducing apparatus may include elements that are not coupled or not continually coupled, such as an apparatus which is held by or fixed to some portion of the user's body, which the user then uses to interact with another portion of the transducing apparatus. Such embodiments may include embodiments employing field effect sensors, which are activated by magnetic or electric fields.

(D11) Transducer mechanical assembly: A 'transducer mechanical assembly' is the more complete assembly into which a basic sensing element is placed in order for it to receive the stimulus to which it is sensitive in response to action from the user and for the purpose of transducing physical phenomena into electrical phenomena.

For example, a basic transducer may be a simple film strain gage; however, this simple film strain gage would likely be mounted to a beam or surface of some sort that bends when interacted with by a user. The beam or surface or the groups of beams and screws and pieces required to mount the strain gage would make up some portion of the transducer mechanical assembly.

More specifically, for the purposes of this invention, a transducer mechanical assembly is a device that directs the user's muscle activity to the transducer. The assembly may also provide a place to mount the transducer, may ergonomically connect the user to the transducer, and may protect the transducer from fluids by environmentally sealing it. One transducer mechanical assembly may hold one transducer, more than one transducer, or multiple transducer mechanical assemblies may be used for one transducer. Further, a transducing apparatus may be comprised of one or any number of transducer mechanical assemblies.

(D12) Electrical signal: As used herein, an 'electrical signal,' when used in the context of passing data from the transducing apparatus to the decision making apparatus, is any appropriate digital or analog signal, such as is known in the art.

Figure 16:
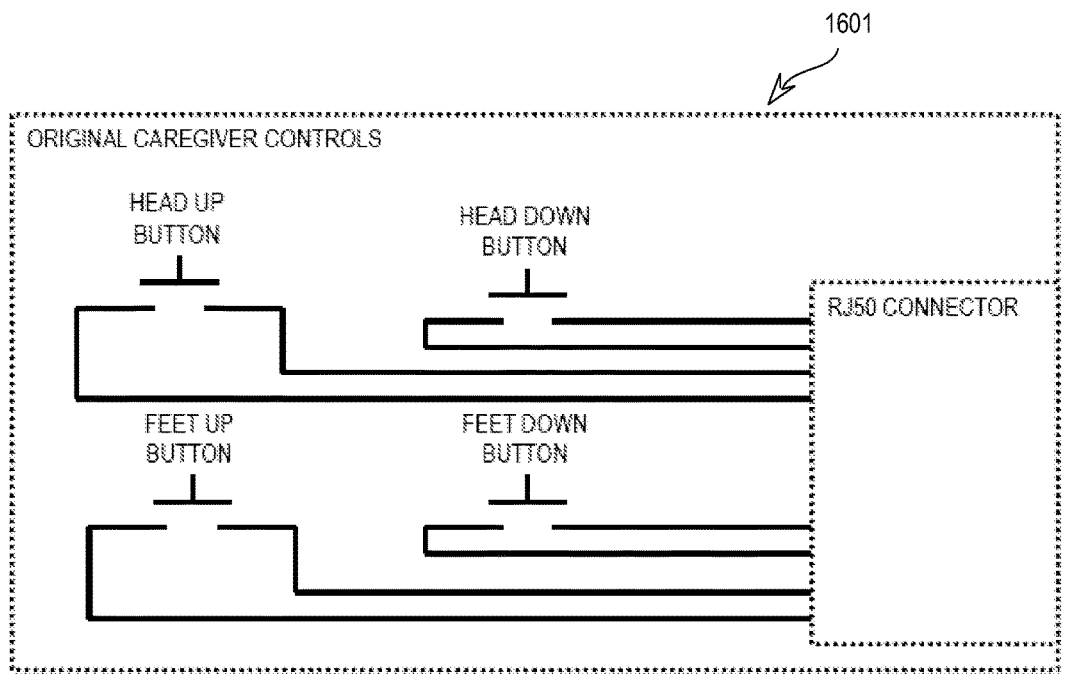
FIG. 16 is an example schematic of an existing hospital bed control pendant.

(D13) Decision making apparatus: As used herein, a 'decision making apparatus' is a structure which is configured to accept electric signals and make decisions therefrom. Such apparatus are well known in the art. One embodiment of a decision making apparatus may be comprised from strictly analog components, such as a circuit using any one or combination of operational amplifiers (op-amps) and comparators as digital gates (see, for example, FIGS. 16 and 17 in Texas Instruments Datasheet SNOSBJ3D, "LM139/LM239/LM339/LM2901/LM3302 Low Power Low Offset Voltage Quad Comparators," accessed Mar. 27, 2014 from http://www.ti.com/lit/ds/symlink/lm139-n.pdf). Such a circuit could, for example, be used to build a state machine in one embodiment of the invention. In various embodiments, the decision making apparatus may also be comprised of any combination of circuits, microprocessors, and other appropriate structures.

In other embodiments, the decision making apparatus may be one or a combination of computing or expert systems, employing known inferential methods, such as Bayesian statistical inference or Monte-Carlo methods. Other appropriate embodiments are further disclosed, and yet others will be known to those of ordinary skill in the art.

Examples of main components that would be expected to appear frequently in decision making apparatus of various embodiments are presented in TABLE 6.

(D14) Adjustable adaptation: As used herein, an 'adjustable adaptation' (or, being 'adjustably adapted') is a configuration of the control apparatus such that the user's physical contact inputs, restricted by the input limitations of the user, are sufficient to effect the user's intended commands directed to the controlled apparatus. Such adaptation is effected by use of one or more adjustable adaptation parameters, and is adjustable at some level to meet the fixed or changing needs of the user. Particular examples of such adaptation will be made obvious in examples of parameters and various embodiments.

(D15) Adjustable adaptation parameter: As used herein, 'parameter' or 'adjustable adaptation parameter' refers to any adjustment which directly or indirectly adapts one or more of the inputs of the control apparatus to the specific input limitations of a user. The control apparatus' sensitivity to any physical contact may be made adjustable by one or more parameters, which may be embodied as mechanical or electrical parameters, which may control various properties (current, voltage, impedance, logical, force, pressure, torque, velocity, acceleration, acoustics, optics, magnetic field, etc.) Parameters employed may include, but are not limited to, any one or combination of the examples given in TABLE 7. Parameters may be set by a user or any person, and may be in the transducing apparatus, the decision making apparatus, or both.

(D16) Control signal: As used herein, a 'control signal' is an electrical or mechanical signal generated by one or more signal generators at the direction of the decision making apparatus for the purpose of controlling one or more functions of one or more controlled devices. Such control signals are well known in the art. Examples of control signals are listed in TABLE 8.

(D17) Signal generator: As used herein, a 'signal generator' is a structure sufficient for generating appropriate control signals at the direction of a decision making apparatus. Such structures are well known in the art. In various embodiments, a signal generator may be output means integral to one or more elements of the decision making apparatus, a digital to analog converter, or any appropriate combination of signal generating structures.

(D18) Transmittance apparatus: As used herein, a 'transmittance apparatus' is a structure which transmits one or more control signals from a signal generator to the controlled apparatus. Such apparatus are well known in the art. Examples include: a simple cable, a USB host controller for USB signals, a UART level shifter for RS-232 signals, a driver and wires for most digital and analog control signals, Ethernet, controller area network (CAN), and a radio and antenna for wireless protocols.

(D19) Grip intensity: As used herein, 'grip intensity' refers to a user's grip and the strength thereof on some portion of a transducing apparatus. A user's grip may be in various positions, such as a power or crush grip (such as is used in a handshake or when gripping pistol-grip handheld electric drills), a pinch grip (such as is used when picking up a book, paper, or coins), or a support grip (such as is used when carrying a bucket of water).

A control apparatus may be adjustably adapted to the input limitations of a user's grip intensity when using grip as a physical contact input. Such adaptations are obvious upon reading the full disclosure, and examples are given in various embodiments, particularly in Example 1.

In some embodiments of the invention, various elements may be physically combined. As one example, the actual physical assembly (such as a circuit board) containing the decision making apparatus may also contain some portion or all of the transducing apparatus (such as a signal generator), and may also contain all or part of the signal generator and some portion of the transmittance apparatus. Various combinations of the different elements of embodiments of the invention as herein defined will be obvious to those in the art as appropriate for the specific application and environment of use.

EXAMPLE EMBODIMENTS

Disclosed herein are examples of particular embodiments of one or more aspects of the invention. This list is by no means exhaustive, and is provided for the purpose of illustrating the scope of the invention and enabling practice of currently preferred embodiments of the invention.

In one embodiment, the user controls one or more controlled apparatus by cycling the decision making apparatus through a plurality of available states associated with various functions of the controlled apparatus. In various embodiments, the controller apparatus may be cycled by advancing one state per input, may continue cycling through available states while a specific physical contact input continues to be given, may cycle through some number of states before stopping, or may cycle continuously until a command to stop is given.

In any of the above described state-based embodiments, the current state can be activated by the user to activate the related function(s) of the controlled apparatus. In various further embodiments, deactivation of the state may be caused by completion of the action initiated by said current state, initiation of a sustainable action which the current state need only activate for a discrete amount of time to cause to be sustainably activated, by cessation of the input representing the activation command, or by receiving an input predetermined to deactivate the current state.

In one embodiment, the transducing apparatus is wholly or partially disposed in one or more transducer mechanical assemblies which are at least partially housings suitable for gripping in a human hand. In a further embodiment, the transducing apparatus is substantially contained in two separate housings suitable for gripping in a human hand and configured to transduce the user's grip intensity as the primary means for directing commands to the controlled apparatus. Still further, the user squeezing one pendant causes the decision making apparatus to advance from a current state to one of a plurality of available states, and squeezing the other pendant causes the decision making apparatus to activate the current state and to maintain it in active state until the user releases or loosens their grip on the state-activating pendant. The grip-sensing pendants are configured specifically to the user's needs so that the grip intensity required to activate the pendants is adjustably predetermined, i.e. preset such that a given grip intensity will activate the pendant, but adjustable to fit the changing needs of the user. The required grip intensity may be the same or different for the two pendants, and is predetermined by setting any number of parameters, as discussed previously. In a further embodiment, the parameters may be set by manual adjustment of a knob, lever, or similar adjustor located on an inconspicuous part of the grip pendant. In an alternative embodiment, the parameters may be set by a remote control. In yet another alternative embodiment, the parameters may be set by a machine-learning algorithm.

In one embodiment, one or more housings comprising transducer mechanical assemblies of the transducing apparatus or any portion(s) of it are chosen to some degree to be fitted specifically to some part of the user's body that the user desires to employ in controlling the controlled apparatus, and thereby assists the user in applying the physical contact inputs necessary for control.

In a further embodiment, the preferred geometry of the housings are chosen using any of the following methods: (i) forming a deformable material, such as modeling clay, putty, plaster, or low temperature plastics, to the user; (ii) forming a deformable object, such as a shape memory viscoelastic object, epoxy filled flexible membrane such as a balloon, Styrofoam filled stress ball, deformable thermoplastic object, or supersaturated solution crystallization handwarmer, to fit the user; (iii) measuring the user, as by three-dimensional image scanning, use of a coordinate measuring machine, computed tomography scanning, magnetic resonance imaging, and crafting a custom geometry from the results; (iv) comparing multiple existing objects to the user, such as common and household items of a potentially desirable geometry, or standard elements (e.g. standard grips, or standard foot pads), and consequently selecting a preferred geometry or combination of preferred geometrical elements to fit the user; (v) any combination of these methods; or (iv) any combination of any of these methods with additional methods.

In one embodiment, the transducing apparatus is comprised of one or more buttons and associated structures, where the buttons are located substantially against the appropriate fingertips of the user (for example, by embedding in hook-and-loop fastened pouches, elastically fastened pouches, adhesive pouches, gloves, or mitts) containing such that the user applies a physical contact input(s) by simply pressing the fingertip against a sufficiently inflexible object, such as a hard surface, the palm of the hand, or another portion of the body.

In one embodiment, the transducing apparatus is configured to provide at least one binary electrical signal to the decision making apparatus.

In various embodiments, the control apparatus is provided with a means of providing feedback to the user, thereby giving them confidence in what will happen when particular commands are given. In a further embodiment, the state-based, dual-pendant, grip sensing embodiment discussed previously is provided with a feedback mechanism that informs the user of their progress in actuating the transducer and also informs the user of the current state, thereby allowing the user to be sure of the effect of actuating the state-activating grip. Examples of potential mechanisms that may be used include: vibration, haptic, audible, and visual.

Various embodiments may be configured to allow a user or users to monitor the status of a controlled device, such embodiment optionally providing feedback of the controlled device's status. As an example, a user may desire to control a door while remaining in a bed. The control apparatus may monitor or communicate with the door to determine whether the door is currently open, closed, or closed and locked, and communicate that status to the user every time the user requests a status change to the door. The feedback may be communicated to the user through a series of buzzes, for example: 1 for open, 2 for closed, and 3 for closed and locked. Alternatively, the status may be communicated upon demand, or communicated continuously, such as through a dedicated light or a visual display.

In one embodiment, the controller is particularly configured to extend the control available to persons affected by loss of muscular or neural function by particularly adapting the transducing apparatus housing, such as described above, to be ergonomically advantageous for activation, and further configuring the parameters to be particularly suited for a patient with such handicaps.

In various embodiments, the controller is configured with a means for storing and accessing parameters for more than one user, thereby allowing the controller apparatus to be advantageously adjusted for multiple persons and used alternately by such persons without complete readjustment of all parameters. Such stored parameters may be unlocked or accessed or both by various known authentication methods, such as personal identification number (PIN) codes, magnetic swipe cards, near field communication (NFD) swipe cards, or 1D or 2D optical bar codes (such as QR codes), as well as by known biometric authentication methods, including fingerprint, retina, weight, or face recognition.

In further embodiments, authentication may be extended to encompass users who are authorized to interact with the control apparatus. For example, different user profiles may be stored, in combination with permissions settings, thereby restricting alteration of settings of the control apparatus and, optionally, the devices it controls, to persons authorized to make such alterations. In this way, doctors, nursing staff, caregivers, and family may adjust respective functions controlled by the control apparatus, but children and visitors may not. Similarly, patients who are capable of adjusting settings may do so, but patients with mental or physical incapability may be protected from accidentally harming themselves through altering certain functions. In some embodiments, the control apparatus may be implemented as a networked control system in a care environment, such as a nursing home or hospital, or may be adapted to home automation for a patient or handicapped person.

In one embodiment, the controlled apparatus include one or more of: motorized hospital beds, motorized wheelchairs, media players, and communication means. Control may be partial or total. In further embodiments, controlled apparatus include one or more of apparatus listed in TABLE 8, as well as substantially equivalent devices.

In various embodiments, multiple physical contact inputs may be used to represent a single intended command, such as a sequence of inputs required to generate a word for output to a display device. In various other embodiments, one physical contact input may be used to represent a plurality of intended commands, such as a single command predetermined to effect both opening a door and sending a welcome message.

In various embodiments, the control apparatus may be an expert system which is continually adapted to the input limitations of a user or users via any combination of manually and automatically adjusted parameters. Such a system may, for example, take the form of a combination of elements of Examples 1 and 7, discussed below: a state-based hospital bed control for a patient suffering from severe arm weakness and hand tremors, with two pendants that allow the user to cycle through available modes (or states) and to activate the current mode. Using machine learning techniques the system continually adjusts the parameters affecting the grip intensity the user must apply to a pendant for actuation. Thus, as the user's strength and tremors vary throughout the day, the system compensates accordingly, adjusting the parameters so that the control apparatus is constantly adapted to the input limitations of the user, even as those limitations fluctuate, and even as the limitations vary between the two hands of the user. Additionally, the parameters may be adjusted manually by a caregiver to, for example, override the automatic adjustment or train the system.

In various embodiments, primary or secondary users are able-bodied persons who desire to extend the control potential available from a limited set of physical contact inputs.

DETAILED DESCRIPTION OF THE DRAWINGS

FIG. 1

This generalized block diagram illustrates selected components of a general control apparatus of the invention. In particular, the transducing apparatus shown here is comprised of blocks 102-106. A user applies a physical contact input 101 to transducer mechanical assembly 102.

Transducer mechanical assembly 102 is one or more components or apparatus, which directs the user's muscle activity to the at least one transducer 103 of the transducing apparatus. Transducer mechanical assembly 102 may also provide a place to mount the transducer 103, may ergonomically connect the user to the transducer 103, and may protect the transducer 103 from fluids by environmentally sealing it.

For some transducers, a transducer excitation circuit 104 provides the electrical stimulation needed for transducer 103 to output an electrical signal. In a particular embodiment, this might include a direct current (DC) voltage supply for a resistive strain gage sensor. Transducer excitation circuit 104 is an optional component, because some transducers do not need any excitation.

Analog signal conditioning 105 is the collection of circuits that prepare the signal to be digitized or otherwise used by the decision making apparatus, represented here by processor or decision making circuit 107. It may typically include attenuation or amplification circuits or both, low pass filters to remove noise above the nyquist limit, high pass filters to remove static signals, reference signals, voltages, currents, self-calibration paths, temperature compensation circuits, circuits to measure environmental factors that affect the transducer (such as cold junction temperature affecting a thermocouple transducer), circuits to linearize a non-linear transducer, circuits to non-linearize the transducer signal (such as to allow both high range and high sensitivity in the normal range of the sensor), or any combination thereof. Analog signal conditioning 105 is an optional component, because some transducers do not need any signal conditioning.

Analog to digital converter 106 digitizes the analog signal into a digital signal that the digital processor or decision making circuit 107 can use. Analog to digital converter 106 is an optional component, because some decision making apparatus can use analog signals directly without converting them to a digital representation.

In this embodiment, the decision making apparatus is comprised of processor or decision making circuit 107. This component chooses whether to enable outputs based on the current or past values of the signals from the transducer apparatus. Processor or decision making circuit 107 may be a digital component such as a microcontroller, field programmable gate array (FPGA), or complex programmable logic device (CPLD), or may be implemented as a set of non-digital analog components such as comparators, operational amplifiers (op-amps), resistors, and metal-oxide-semiconductor field-effect transistors (MOSFETs).

Signal generation 108 (which may also be an external interface circuit, and may include components such as relays, a 36V logic signal, etc.) creates control signals as directed by the decision making apparatus, which are transmitted to controlled devices 109.

Feedback apparatus 110 is an optional component that may be provided to give feedback 111 to one or more users. Feedback 111 may be, for example, a notification of which state is currently available, which state was just activated, other available states, results of activation of a state (such as a yes/no answer from a patient user to a caregiver user), or any combination thereof. Examples of components of feedback apparatus 111 include LED's, buzzers, and tactile stimuli.

FIG. 2

This generalized block diagram illustrates selected components of a particular grip-sensing embodiment. Users apply physical contact inputs as muscle movement 201 to a transducing apparatus (components 202-206) comprised of transducer mechanical assemblies particularly configured to be gripped by a user and therefore referred to as grip mechanicals 202. Appropriate transducers 203, excited, if applicable, by transducer excitation 204, produce electrical signals which are conditioned, if necessary, by analog signal conditioning 205 before being digitized, if necessary, by analog to digital converter 206. Processor or decision making circuit 207 then chooses whether to enable outputs based on the current or past values it receives.

Signal generation 208 creates control signals as directed by the decision making apparatus, which are transmitted to controlled devices 209.

Feedback apparatus 210 is an optional component that may be provided to give feedback 211 to one or more users, as described in relation to FIG. 1.

FIG. 3

This exploded view of one of two hand-held pendants comprising the transducing apparatus in a grip-sensing embodiment is a particular implementation of a portion of the embodiment particularly discussed subsequently in Example 1. A top housing shell 302 and bottom housing shell 306 are assembled together with a bolt 301 and nut 307, and comprise a transducer mechanical assembly which is an ergonomic housing for a transducer and related components designed to be activated by a user gripping the housing and thereby squeezing the top housing shell 301 and bottom housing shell 302 towards each other.

Between top housing shell 301 and bottom housing shell 302 is mounted a bendable element 303, such as a metal beam, so that the end of bendable element 303 closest to assembly bolt 301 is fixed sufficiently securely, but the opposite end of bendable element 303 is sufficiently free to bend when deflected by pressing element 308.

Quarter-bridge strain gage 304, or other suitable flex sensor, is mounted on bendable element 303 such that as bendable element 303 is deflected, strain gage 304 is stretched, changing its resistance. This resistance is output to a decision making apparatus, not shown. Vibration buzzer 305, which may only be in one of the two grip units, is disposed inside the housing, and is activated upon the resistance, change in resistance, or other suitable output crossing a predetermined threshold for activation, controlled by the decision making apparatus, which is connected to strain gage 304 in a manner configuring strain gage 304 as a quarter bridge.

This particular embodiment has been advantageously used by a patient with advanced ALS disease and severe loss of dexterity and muscle control to control a hospital bed after losing the ability to manipulate standard hospital bed controllers and communication means.

FIG. 4 and FIG. 5

These figures depict an isometric view of the top housing shell 302 and bottom housing shell 306 discussed previously.

FIG. 6

This block diagram of a configuration of a control apparatus, controlled device, and associated structures discussed in Example 1 below depicts a two-pendant grip-sensing control apparatus configured to control a hospital bed. User's left hand 601 holds a strain gage-based grip unit 602, comprising transducers and related structures disposed in a housing specifically fitted to be advantageously gripped by the user's hand. Similarly, user's right hand 605 holds a similar strain gage-based grip unit 603. Disposed in an enclosure 617 located underneath the hospital bed are components 603-610. The transducer apparatus is comprised of components 602, 603, 606, and 607. Excitation and signal conditioning components 603 and 607 provide excitation to the strain gages in grip units 602 and 606, respectively, and condition the electrical signals from the strain gages in grip units 602 and 606, respectively, before the electrical signals are passed to the decision making apparatus. The excitation and signal conditioning components 603 and 607 are connected to their respective grip units 602 and 606 by cables 612 and 613, respectively.

Arduino boards serve as analog to digital converters 604 and 608, digitizing the conditioned analog electrical signals from excitation and signal conditioners 603 and 607, respectively. An Arduino-based microcontroller and associated software comprises the decision making apparatus 609. Decision making apparatus 609 causes appropriate signals from grip unit 602 to cycle through available states in a state machine, representing different functions available for activation, and appropriate signals from grip unit 606 to activate the current state, thereby activating the currently represented function (such as adjusting some portion of the bed or ringing a request-for-help bell).

When a state is activated, decision making apparatus 609 causes signal generator 610 to generate and condition a control signal appropriate to the respective control input, such as hospital bed control inputs 611. The control signals are conveyed to the appropriate control input via cable 614, comprising the transmittance apparatus.

Decision making apparatus 609 further causes signal generator 610 to activate a buzzer 616, located in grip unit 606 and connected via cable 615, upon successful advancement of the current state to the next available state, thereby providing feedback to the user of the current state available for activation.

FIG. 7A, FIG. 7B, and FIG. 7C

This illustration of one portion of the transducing apparatus in a grip-sensing embodiment, such as discussed in Example 1, shows the operation of the grip unit by a user's hand. FIG. 7A illustrates the grip unit in an unsqueezed, or unactivated state. Note how the two halves 701 and 702 of the housing are not attached at one end and are naturally somewhat separated at that end. This separation is due to pressing element 704 resting against bendable element 703, which is in its naturally substantially unbent state.

FIG. 7B illustrates the grip in a squeezed, or potentially activated state. Note how the two halves 701 and 702 of the housing are substantially unseparated, causing pressing element 704 to deflect bendable element 703, causing it to bend into housing half 702. When squeezed such that a flex sensor (not shown) mounted on bendable element 703 outputs an electrical signal sufficient to cross a predetermined activation threshold, the decision making unit either advances the current state (and also causes the buzzer to be appropriately activated) or causes the function represented by the current state to be activated, depending on the grip unit which is being squeezed.

FIG. 7C illustrates the two halves 701 and 702 of the grip unit housing in a squeezed state in a user's hand.

FIG. 8

This schematic of the microcontroller and associated signal conditioning in a grip sensing embodiment, as discussed in Example 1, comprises the decision making apparatus for this embodiment, analog to digital converters of the transducing apparatus, and the signal generator.

Electrical signals 809-10 from the transducers in the grip units are digitized by analog to digital convertors 801 and 802 before being passed to the decision making apparatus. The thresholds (comprising some of the parameters for this embodiment) for each grip are increased or decreased via buttons 803-806. This allows a user (typically a caregiver) to adjust the thresholds appropriately for the primary user (typically a patient). Digital outputs 807 are provided for a feedback buzzer and for each function available for the user to control, in particular the available bed control inputs (such as raise and lower head, raise and lower foot, and raise and lower entire bed) and an electronic bell. Appropriate signal conditioning 808 for each output is also provided. I2C port 811 provides a connection to an LCD display for showing grip strength and the currently chosen thresholds.

Figure 9A:
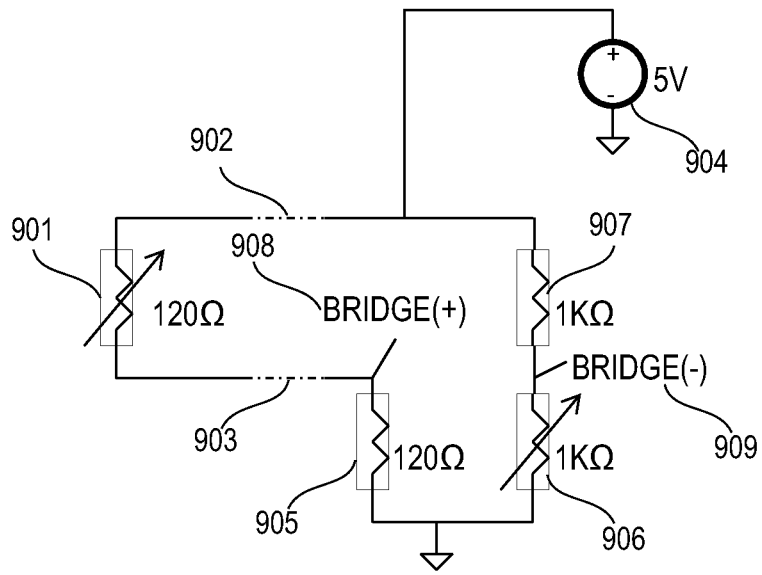
FIG. 9A and FIG. 9B are schematics of the signal conditioning means in a grip-sensing embodiment.
Figure 9B:
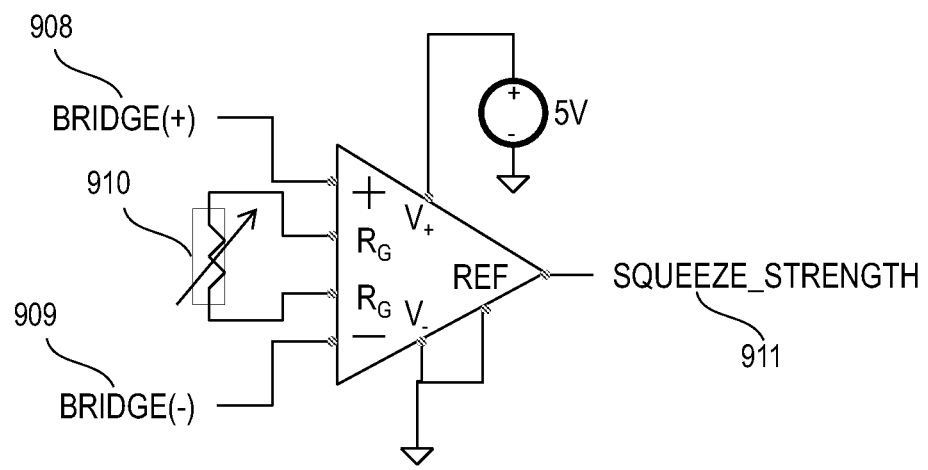

FIG. 9A and FIG. 9B

This representative schematic of the various signal conditioning means in the transducing apparatus of a grip-sensing embodiment, as disclosed in Example 1, shows only the signal conditioning pertaining to one grip unit.

FIG. 9A illustrates the circuit that provides for completion of the Wheatstone bridge and excitation of the transducer. In particular, a 120 Ohm quarter-bridge element 901 is used within the grip unit's housing, and connected to the remainder of the signal conditioning means via cables 902 and 903. Excitation (5V) 904 is provided to the transducer. The Wheatstone bridge is completed with 120 Ohm resistor 905, 1 kOhm resister 905, and 1 kOhm variable resistor 906. Resistors 905 and 906 form an adjustable half-bridge that allows for offset nulling prior to gain.

FIG. 9B illustrates the circuit that provides gain and differential to single-ended conversion. The two legs of the bridge 908 and 909 are connected to the analog to digital convertor, which provides element 910 for adjustable gain to allow for increased resolution for digitizing, adjusted for the grip strength of the user. The digitized electrical signal is output at terminal 911, with a range of 0 to 5V, corresponding to the strength of the squeeze.

Specific values of circuit components and electrical signals are provided only for illustrative purposes, and countless variations within the scope of this disclosure and claims will be readily apparent to those skilled in the art.

FIG. 10

This schematic 1001 illustrates the decision making algorithm of the decision making apparatus in a grip-sensing embodiment as discussed in Example 1. In particular, this algorithm provides for five states corresponding to four bed controls and one bell, and the two adjustable thresholds (one for each grip unit). Further, the schema for the vibration buzzer to notify the user of which state is currently available for activation is provided. Of course, countless variations of this algorithm within the scope of this disclosure and claims will readily be apparent to one skilled in the art.

FIG. 11

This schematic 1101 illustrates a generalized representation of activation and deactivation of a state in a stateful embodiment. An appropriate input from the user causes the state to be advanced until a desired current state is selected, but not activated. Upon further appropriate input from the user, which may be identical to or different from the input provided to advance the states, the current state is activated. Upon activation, the function controlled by that state occurs until deactivation of the state. After deactivation, the current state remains available until further input causes the state to advance. In some embodiments, the decision making unit may be configured to cause the state to advance automatically upon deactivation of the current state.

In various stateful embodiments, a user may use one or multiple input means of the transducing apparatus to advance the current state to a state representing the function(s) desired. The user would then use the same or different input means to activate the current state. Deactivation would occur, for example, when the user ceases applying the input, upon a subsequent input from the user, upon completion of the action initiated by the current state, upon a certain amount of time passing, or upon input from another source.

FIG. 12

Figure 11:
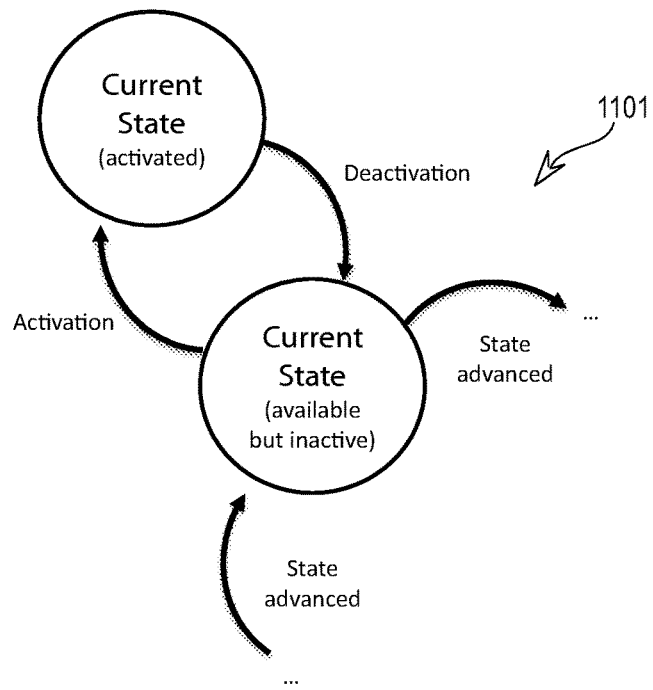
FIG. 11 is generalized representation of activation and deactivation of a state in a stateful embodiment.
Figure 12:
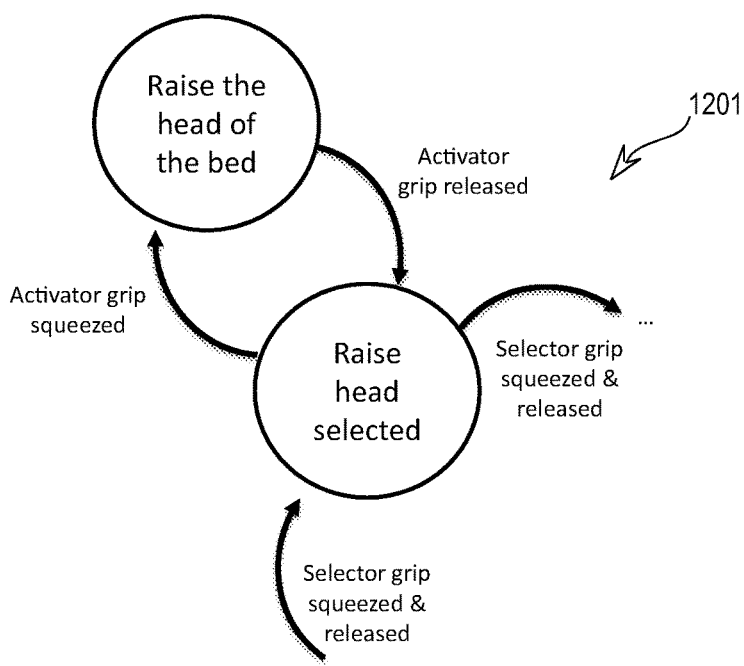
FIG. 12 is an exemplary illustration of activation and deactivation of a state in a stateful embodiment capable of raising the head of a hospital bed.
Figure 13:
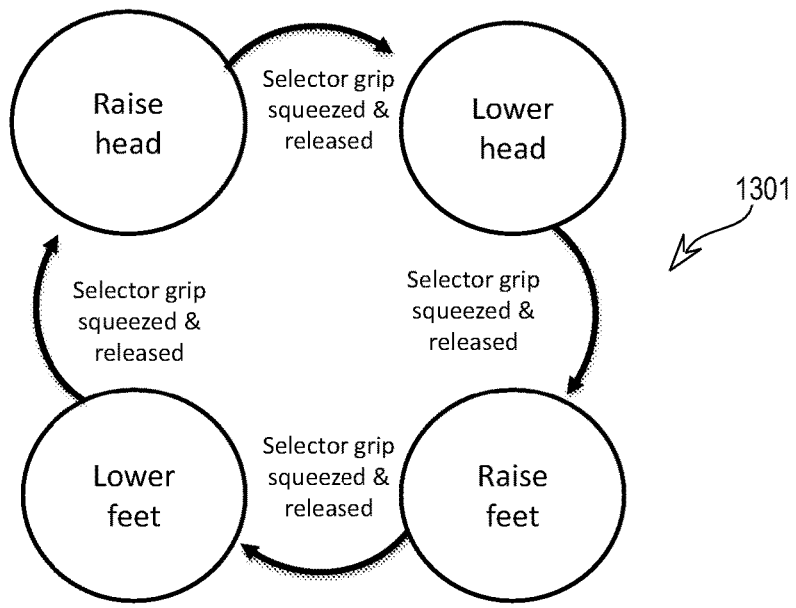
FIG. 13 is a state machine drawing of states available to the user(s) in an embodiment which controls a hospital bed.
Figure 14:
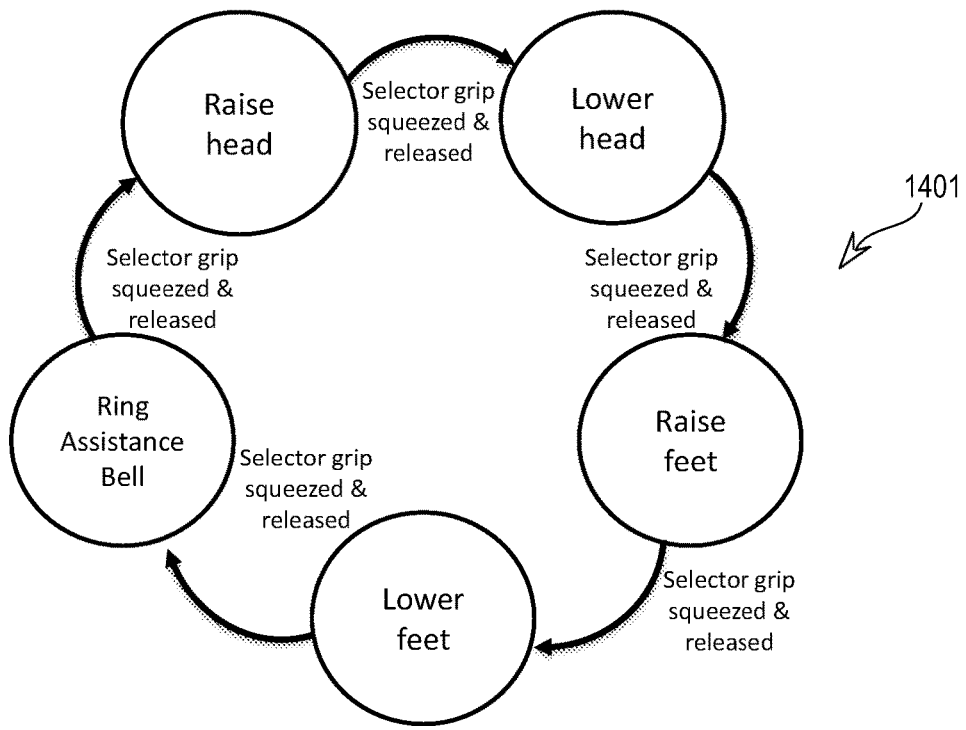
FIG. 14 is an expanded state machine drawing of states available to the user(s), including additional control of functions possibly needed from the bed, such as ringing a bell, in an embodiment which controls a hospital bed.

This schematic 1201 illustrates activation and deactivation of a particular state, as discussed generally in relation to FIG. 11, in an embodiment disclosed in Example 1. A current state, representing raising the head of a hospital bed, is selected using the selector grip. The activator grip is then used to activate the current state, thereby causing the head of the bed to be raised. The state is deactivated when the user ceases squeezing the grip, thereby causing the head of the bed to cease being raised. The current state continues to remain available for activation until the state is changed by further activation of the selection grip by the user.

FIG. 13

This state machine drawing 1301 depicts some of the states available to the user(s) in a particular embodiment which controls a hospital bed. In the embodiment in Example 1, for example, each time the patient squeezes the selector grip, the next state is selected and the vibration buzzer gives feedback by buzzing a recognizable pattern for that state. In one implementation, the buzzer might buzz once for the first state, twice for the second state, three times for the third state, and so on. As discussed previously, the patient activates the selected state by squeezing the actuator grip, thereby resulting in actuation of the motors or actuators on the hospital bed corresponding to the current state. To deactivate the selected state, the patient ceases squeezing the actuator grip. Depicted here are four example states, corresponding to lower and raising the head and foot of the bed.

FIG. 14

This expanded state machine drawing 1401 of states available to the user(s), depicts including additional control of functions possibly needed from the bed, such as ringing a bell, in an embodiment which controls a hospital bed, such as discussed in Example 1. The control apparatus may interface with other electronics, other than the hospital bed, which are required while the patient is in the bed. These other electronics may include, as shown here a Request Help bell.

FIG. 15

This schematic shows one example of a cost optimized version of an embodiment capable of interfacing to an existing hospital bed, such as is discussed in Example 1, and depicts elements of the system interfacing to the patient and to the hospital bed. Control logic element 1502 (comprising in part the decision making apparatus) measures grip strength from strain gages 1511 in selector grip 1507 and actuator grip 1510. Control logic element 1502 then causes a signal generator to output to vibration buzzer 1509 to indicate the current state to the user. The control apparatus interfaces to hospital bed 1504 through existing hospital bed control box 1506 by connecting into control mixer 1503, which is connected to existing hospital bed control connector 1505. The caregiver can adjust additional settings using existing caregiver controls 1501, which are also connected to existing hospital bed control box 1506 through control mixer 1503.

FIG. 16

Figure 15:
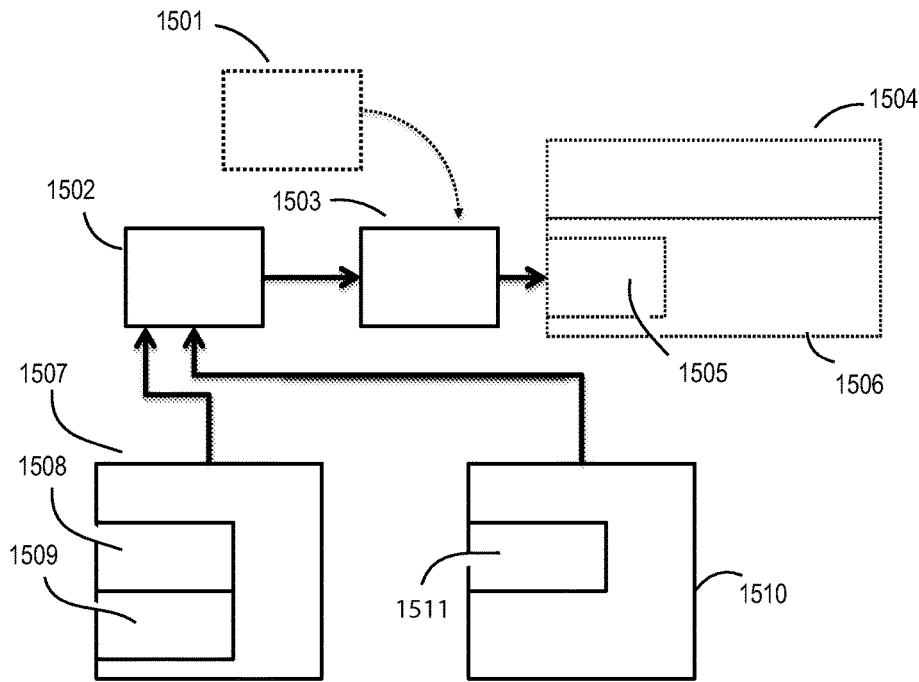
FIG. 15 is an example schematic showing a cost optimized version of an embodiment capable of interfacing to an existing hospital bed.

This example schematic illustrates an existing hospital bed control pendant 1601, such as is replaced by the embodiment shown in FIG. 15. Such a control pendant does not use a state machine. The buttons require finger dexterity to select the correct one. The strength required to activate each button is not adjustable and, therefore, cannot be changed to match the strength of the current user, or continually adjusted as the patient's strength changes.

EXAMPLES

The preceding disclosure will be further understood by the use of several examples of specific embodiments of apparatus and methods which are disclosed solely for illustrative purposes, and should not be construed as limiting in any way. Further examples of other embodiments of the invention will readily present themselves to persons skilled in the art.

Example 1

In accordance with one embodiment, a control apparatus is provided to enable a person suffering from severe loss of dexterity or muscle control (such as one afflicted with ALS) to extend control of a hospital bed and, optionally, other devices and functions. Instead of a normal hospital bed controller, typical of which is a control pendant with many on/off style binary push-buttons, the patient holds in each hand a single unit configured to transduce the patient's grip. These two grip units, which comprise the transducing apparatus, measure the amount of grip from the patient, and can be adjusted to match the patient's strength.

One grip transducing unit selects states in a state machine, while the second grip transducing unit actuates the selected state. This allows two adjustable, comfortable grips to replace the buttons on a traditional control pendant that are hard to use for many patients with limited dexterity or muscle control. This also lengthens the amount of time a patient may be able to control his or her own comfort, and improve quality of life for both patient and caregiver.

Further, a vibration, haptic, audible, or visual feedback indicates to the patient which state is currently selected. A means of providing feedback to the user of their progress in actuating the transducer and, optionally or additionally, of their current state, may often be advantageous in this and similar situations to allow the patient to be sure of what will happen upon actuation of a grip. In many cases, vibrational feedback may be particularly advantageous in bed usage since tones may wake up neighbors or caretakers, and visual feedback may not be practical at night, in the dark, for blind users, or due to high implementation costs.

In operation the patient holds the selector grip with one hand and the actuator grip in the other. The caregiver places the grips in the patient's hands, and the patient squeezes the selector grip through several states to demonstrate to the caregiver that it is properly positioned. The patient knows which state is selected by listening or feeling the feedback vibration buzzer. The patient then squeezes the actuator grip, causing the selected portion of the bed to move (e.g. lifting/lowering the head, lifting/lowering the entire bed, or lifting/lowering the foot), to demonstrate to the caregiver that it is properly positioned. The caregiver now knows that the patient is in control, and may move on to other tasks.

At this point the patient is free to adjust the bed as desired. If the patient requires additional assistance, he or she may use the selector grip to select an optional state which controls a communication device, such as a nurse's call or I-need-help bell, and then activate the device using the actuator grip to call the caregiver back for assistance.

The decision making apparatus, primarily comprised of a control logic element, measures the grip force and may make use of signal processing performed in the transducing apparatus or in the decision making apparatus to filter out patient tremors or shakes such as is common with Parkinson's disease, or high baseline grip force muscle tension such as is common with ALS. Specific signal processing filters may include infinite impulse response (IIR) or finite impulse response (FIR) filters to reject tremors from activating or selecting states. The caregiver may also adjust the grip force threshold or hysteresis for the grip sensors. Adjustability may be alternatively or additionally provided by mechanical adjustability of the separation between two halves of a grip unit, which may be controlled by a combination of shimming and adjustable separation to create an activation force matching the strength of a patient. Further, the parameters may be used to set the grip intensity for one grip different than the other. As alluded to previously, the parameters may be incorporated directly into a circuit or algorithm, may be mechanically set, may be adjusted by various users including patients, caregivers, installers, and technicians, or may be dynamically adjusted by an algorithm in response to one or more metrics.

Figure 10:
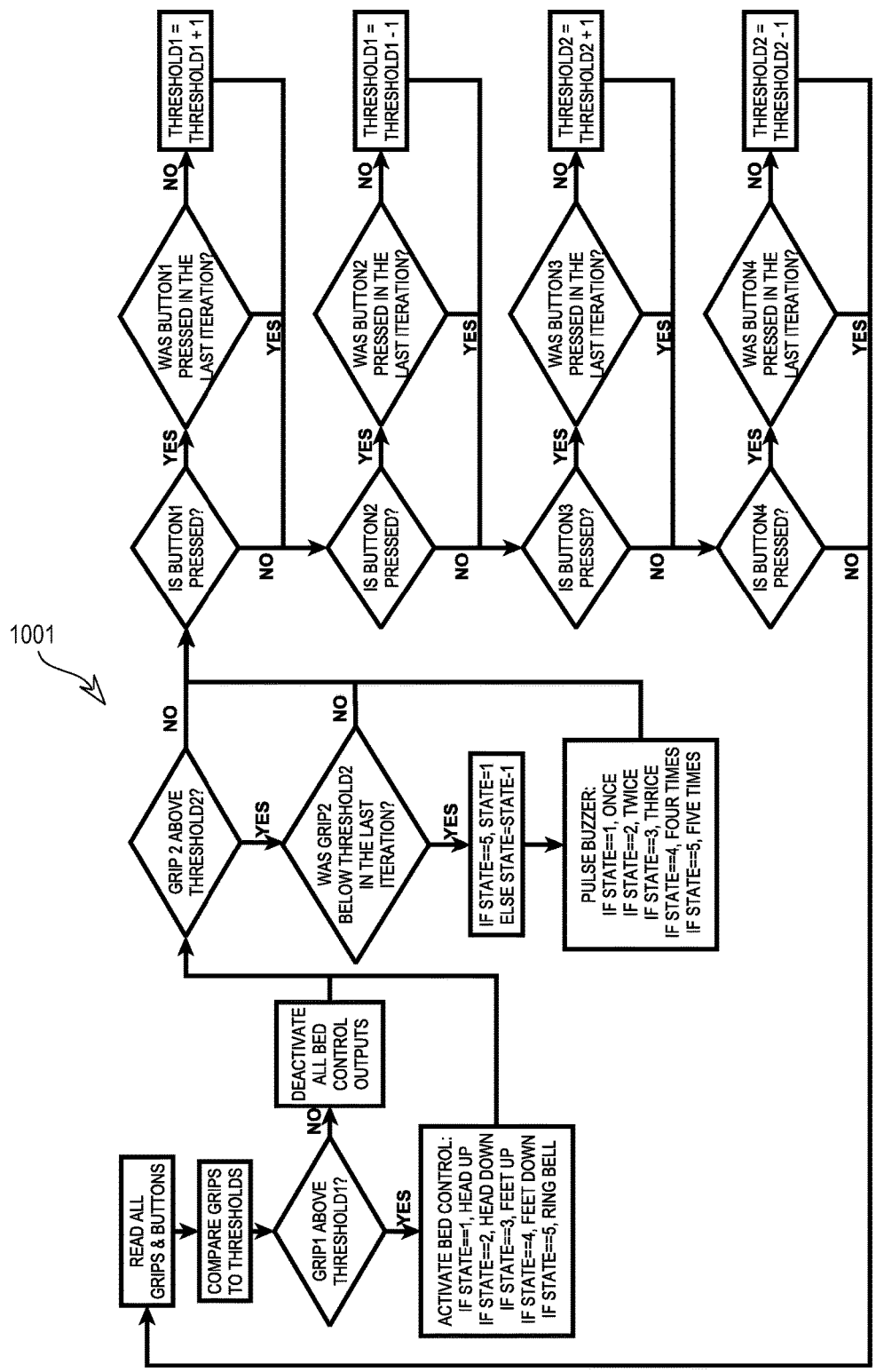
FIG. 10 is a schematic of a decision making apparatus in a grip-sensing embodiment.

Two implementations of this example have been completely built and performed satisfactorily for a patient. Specific implementations of the features and elements of the embodiment are given in TABLE 9. One implementation was built using National Instruments cRIO hardware and compatible LabVIEW software running a custom LabVIEW algorithm illustrated in part by the LabVIEW FPGA and LabVIEW RT code. The other implementation was built using an Arduino-based decision making apparatus and compatible components, represented in part by the flowchart of FIG. 10 and in part by the Arduino code (similar to the C programming language) algorithm in APPENDIX 1. The cRIO implementation may be represented by a substantially identical flowchart, except that buttons were not utilized to change thresholds. The Arduino and cRIO implementations employed different hardware to achieve a substantially equivalent solution, connected to the same sensors and to the same bed control interface. The algorithms were written in two significantly different languages, but performed substantially identical functions.

Example 2

In accordance with one embodiment, an analog force sensing button and adjustable threshold circuit may be implemented to replace a standard push button switch, such as is used to partially control the MOBI2 communication device sold by Zyteq Pty Ltd. Such an embodiment would be helpful, for example, to a user who could actuate their thumb more advantageously than their whole hand. In particular, the transducer apparatus may include a FSR-based pressure sensor to transduce a physical contact input of pressure applied by the user's thumb. One implementation of this example has been completely built and performed satisfactorily for a patient.

Example 3

In accordance with one embodiment, the transducing apparatus is configured to make use of a squeeze bulb or squeeze balloon, serving the part of a transducer mechanical assembly. This may be a liquid or gas filled ball or balloon which the user holds in a hand, under an armpit or knee, or with some other joint and squeezes. The associated transducer could be, for example, a gas pressure, liquid pressure, or flow sensor. One examples of such a transducer is a strain gage on a diaphragm, resulting in a bridge-based sensor with an analog output, and thereby configured as a pressure transducer. As the user squeezes, the pressure in the bulb increases and is measured by the pressure transducer. The squeeze balloon may be generally bulb-shaped, or may have geometrical features (such as a ridge, ledge, indentation, out-pouching, non-symmetrical 3D shape, custom-fitted shape, etc.) which serve to further adapt the transducing apparatus to the input limitations of the user. Further, the materials (elastomers such as nitrile and other butadiene-based rubbers, polyurethane elastomers, silicone elastomers, or natural rubber) and material properties, such as hardness (for example, Shore OO 0-100 or Shore A 0-100), may be chosen to be adapted for the patient.

Example 4

In accordance with one embodiment, the transducing apparatus is configured to make use of a glove, similar to a Power Glove Nintendo controller, which senses finger position or tension. Transducers for such an embodiment include, for example, a displacement transducer such as a string potentiometer or linear variable differential transformer (LVDT) mounted on a limb, or mounted on a piece of equipment near the user and tethered to an extendable joint of the user's body such as fingertips (hinging on the hand), a wrist (hinging on the arm), the end of a foot (hinging on the ankle) or the chin (hinging on the neck), such that movement of the joint produces displacement between the location where the sensor is mounted and the location where the sensor is tethered to the users body. Similar results may also be accomplished without any direct attachment to the user's body, such as by placing an LVDT underneath a hinged panel that a user's foot rests upon. Thus, by flexing the foot, a user causes displacement of the hinged panel, which is measured by the LVDT.

Example 5

In accordance with one embodiment, the transducer apparatus is configured to make use of a photodetector with gradient interrupter, similar to the system used in a guitar expression pedal. This type of transducer would transduce rotational movement, such as twisting the wrist or head, or extending the tip of a foot, and functions by having a hinge on an axle that the user has the ability to twist or rotate about its axis. On the same axle there is a disc with a gradient of translucence ranging from a section that allows substantially all light to pass through to a section that is opaque. This disc has a light source on one side of it and a photodetector on the other side of it. Therefore, when the axle rotates as the user twists it, the photodector senses a change in the light intensity. Again, the axle does not have to be directly connected to the users body, but can be indirectly attached, such as through a panel that rests on some movable part of the user's body. An example of such a configuration would be a panel under the foot that is hinged by an axle at the heel of the user's foot, with the axle housing the disc and transducer. A control apparatus that utilizes such a system has the advantage of ruggedness and the ability to be easily waterproofed with a glass or plastic enclosure around the transducer elements.

In an alternative configuration, an axle is located along the length of a user's elbow, extending past the elbow, such that the transducer is located and attached to the hand such that rotation of the user's wrist causes the axle to twist.

In another embodiment, the transducing apparatus contains a non-optical transducer, such as a hall-effect sensor mounted in a fixed position near the axle, and a magnet attached to the axle in such a way that rotation of the axle causes the magnet to move closer or further away from the hall-effect sensor. Again, such a configuration has the advantage of being easily enclosed so as to provide ruggedness in environments where fluids are present.

Example 6

In accordance with one embodiment, the transducing apparatus is comprised of a grid or array of transducers, examples of which include FSRs, capacitive touch sensors, and temperature sensors. Such an embodiment is especially useful for users with poor fine motor skills, because only one element of the grid needs to receive input from the user. Thus, difficulty in alignment of the user with the transducing apparatus is minimized, allowing a user with input limitations (such as limited dexterity or muscle control) to actuate the transducing apparatus more reliably.

In yet another embodiment, a touch sense monitor is employed in place of the touch array. This configuration would be comprised of several or even a very large number of sensors in a line or an array on a structure capable of being pressed or held against a movable body part. Each of the sensors is measured either individually with algorithm based decision making detecting intended commands (for example, detecting an intended 'click'), or as a sort of 'OR' structure, such as having a string of FSRs in parallel to each other, such that a change in any element causes a net change in the total resistive element. In a further embodiment, economically feasible transducers are used, thereby providing the added benefit of reducing costs, as only a single analog to digital converter is required to effectively measure, simultaneously, changes in a large number of sensing elements. Thus, almost any motion of the body part against the panel or surface can be measured as a change by at least one of the sensors.

Further embodiments include three-dimensional configurations, examples of which include a grip fitted to the hand, having touch sensors disposed in multiple locations, any touch sensor being able to detect an increase in grip pressure from substantially any part of the user's hand.

Example 7

In accordance with one embodiment, machine learning (ML) techniques are incorporated into the decision making apparatus. Examples of embodiments incorporating ML techniques include: dimensionality reduction algorithms which identify principal components from multidimensional sensor data, classifier algorithms which determine the intent of the user from multiple sensor data points or multiple sensors, and clustering algorithms which identify data for training sets and may adjust parameters of a classifier algorithm.

Other embodiments employing ML techniques include configurations providing a user with a variety of sensor types for transducing gross muscle movements, fine muscle movements, or both, as well as providing sensors adapted specifically to various body geometries. The decision making apparatus employs ML techniques to aggregate sensor data to determine intended outcomes of various events. In one embodiment of such a system, individual finger, analog force sensors are input to principal component analysis which reduces 5 individual fingers to a single principal component indicating grip.

In another embodiment of such a system, data from the individual finger transducers is input to a support vector machine (SVM) classifier to determine whether the aggregate of multiple sensors is in the activated state or the not-activated state.

In another embodiment, a user may be asked to attempt to produce a series of desired outcomes to generate training data, or an ML clustering algorithm such as k-means may also be used to look at prior sensor data and generate training data without additional user input. The training data may be used to adjust parameters on the decision making apparatus. ML technology allows the embodiment to automatically adapt as the user's condition worsens, improves, or changes in other ways.

As ML technology continues to advance, further embodiments using these and similar tools will become increasingly available and feasible and will allow a broad range of possible sensors to be deployed simultaneously to a user, with minimal foreknowledge by a caregiver or user as to what transducers will be most effective for a user to control devices with. Therefore, in some embodiments, available transducers are deployed simultaneously and the algorithm in the decision making apparatus decides what signal(s) and what qualities of a signal are pertinent to the decision making process.

Example 8

In accordance with one embodiment, the user holds some portion of a transducer mechanical assembly, such as one configured as a squeezable grip shaped to fit in the human hand, and squeezes to select a letter of the English alphabet. The decision making apparatus highlights on a visual feedback (or, alternatively, in a voice feedback or vibration feedback) each of the twenty-six letters of the alphabet, plus the space character (twenty-seven characters in all), in a loop which completes a cycle every thirty seconds. The decision making apparatus then records the amount the transducer is activated, corresponding to the time interval of each letter, into a twenty-seven element array. At the end of each thirty second loop, a new array is generated. The decision making apparatus compares the Hamming distance (serving as the branch metric) of the accumulated twenty-seven element arrays to a dictionary of words accessibly by or incorporated into the decision making apparatus. When the normalized Hamming distance between the arrays and a dictionary word drops below a threshold, that word is directed to the transmittance apparatus and the accumulated twenty-seven element arrays are reset. In alternative embodiments, the array may represent any desired set of characters or symbols, including numerals, foreign languages, technical symbols, or pictorial elements. In similar embodiments, an analog transducer enables a higher accuracy decoding of the user's intent similar to the Viterbi algorithm's soft decision decoding, and employing the squared Euclidean distance as the branch metric instead of the Hamming distance.

The embodiments described in the present example, and equivalent embodiments, can offer the advantage to the user of a control apparatus more tolerant of input errors, allowing errors to be more easily corrected. In some embodiments, the control apparatus may additionally be configured to scan more quickly through a character set while minimizing the disadvantage of routinely missing letters due to higher scan speeds and thereby reducing the need to start over or correct spelling, thus, facilitating communication by users with severe handicaps.

The invention claimed has been herein disclosed sufficiently for persons skilled in the art to comprehend and practice. The various embodiments, examples, and illustrations disclosed herein, while representing the best and various alternative modes of carrying out the invention as currently contemplated by the inventors, are by no means limiting or exhaustive, but serve as an aid to comprehending the full nature and scope of the invention. Various other embodiments will become apparent which fall within the scope of this disclosure and claims.

TABLE 1

EXAMPLE INPUT LIMITATIONS FOR VARIOUS POTENTIAL USERS

| Example Input Limitation | Example Typical Control Means | Selected Possible Cause(s) [1] | Type(s) [2] |
| --- | --- | --- | --- |
| Loss of speech/ slurred speech | Normal communication; voice activated control | MS, ALS, S, GBS, BO, M, N | 1 |
| No use of feet | Foot pedal | AL, AMP, I, MD, ALS, GBS, PI, M | 1 |
| Finger press strength of 0.1N | Button(s) with minimum activation force of 1N | MS, CP, MD, M, N | 3 |
| Unable to lift hand, but can flex fingers | Panel of buttons (e.g. remote control) that require finger flexing & hand movement | MS, I, ALS, P, PL | 2 |
| Shaking or trembling hands | Fixed-activation threshold squeeze-activation bell/alarm | PD, ALS, OT, BT, MS, AG, ET, S, PA, CP | 4 |
| Vision loss | Eye-tracking device | MS, BI, EI, SB, GBS, MG, BO, PI | 1 |
| Debilitating pain preventing fine motor control in hand | Knob-based input device, keyboard | A, RSI, I, SX | 2, 3, or 4 |
| Hands or feet occupied | Hand controls or foot pedals | Able user | 1 |
| Arm in a sling or cast | Keyboard or mouse | I, SX | 2 |
| Weak grip | Grip-based game controller | CD, S, MG, BO | 3 |
| Limited control of head motion | Head-mounted stick, stick held in mouth | P, I | 2, 3, or 4 |
| Weak to no control of legs | Knee-activated device | SB, SCI, SX, BO | 1, 2, 3, or 4 |
| Unable to raise arms | Wall-mounted lever | PM, DM, PI, CD | 1 |
| Loss of hand function | Hand activated buttons | P, M, RSI, SX, PI, ALS, AL | 1 |

[1] Abbreviations used: absent limb (AL), aging (AG), amyotrophic lateral sclerosis (ALS), amputation (AMP), botulism (BO), brain injury (BI), brain tumor (BT), various cardiac disorders (CD), cerebral palsy (CP), dermatomyositis (DM), essential tremors (ET), Guillain-Barre syndrome (GBS), injury (I), multiple sclerosis (MS), muscular dystrophy (MD), myasthenia gravis (MG), myopathy (M), neuropathy (N), overactive thyroid (OT), palsy (PA), paralysis (P), Parkinson's disease (PD), poisoning (PI), polio (PL), polymyositis (PM), repetitive strain injury (RSI), arthritis (A), spina bifida (SB), spinal cord injury (SCI), stroke (S), and surgery (SX).
[2] The types of input limitations (D3) that make a user's physical contact input(s) (D2) incompatible with a control means for a controlled apparatus (D4), as discussed above, are:
(1) different nature of inputs,
(2) insufficient variety of inputs,
(3) insufficient intensity of inputs, and
(4) insufficient distinctness of inputs.

TABLE 2

EXAMPLE TRANSDUCABLE (ELECTRICALLY MEASURABLE) PHYSICAL CONTACT INPUTS

| Physical Contact Input [units] | Typical Value | Typical Range |
| --- | --- | --- |
| FORCE/STRAIN | | |
| Power grip by hand [N] | 5-20 | 0.5-200 |
| Push/pull by hand [N] | 10 | 0-100 |
| Leg/foot press [N] | — | 0.5-1.1E3 |
| Finger touch [N] | — | 0-110 |
| Balloon squeezed by hand [MPa] | 0.1-0.7 | 1E-6-1.5 |
| Torque applied by hand to a smooth, 1 in diameter knob [N-m] | 0-0.5 | 0-20 |
| CONTACT | | |
| Thermal contact with skin [1] [° C.] | — | 20-40 |
| Finger touch (see above) | — | — |
| Blocking of light | — | — |
| DISPLACEMENT | | |
| Displacement by finger [cm] | — | 1-15 |
| Displacement by hand/foot [cm] | — | 1-35 |
| Displacement by arm [cm] | — | 1-105 |
| Displacement by leg [cm] | — | 1-200 |
| Displacement by head [cm] | — | 1-155 |
| MOTION | | |
| Rotational acceleration of wrist [G] | — | 0-85 |
| Rotational acceleration of shoulder [G] | — | 0-65 |
| Acceleration of hand [G] | — | 0-110 |
| Acceleration of hand [cm/sec/sec] | — | — |
| Speed of hand [cm/sec] | — | — |
| Flexion/extension of wrist [degrees] | −60-60 | −90-90 |
| Flexion/extension of foot [degrees] [2] | −20-40 | −45-90 |
| Lateral bending of neck [degrees] | −45-45 | −90-90 |
| Rotation of neck [degrees] | −80-80 | −120-120 |
| Flexion of knee [degrees] | 0-150 | 0-175 |
| Flexion of elbow [degrees] | 0-150 | 0-175 |

[1] Estimated temperature values are at point of contact. Actual temperature seen by sensor may vary based on transducer mechanical assembly (D11) setup.
[2] Negative angles correspond to dorsi-flexion (pointing the toes toward the head), positive angles correspond to plantar-flexion (pointing the toes away from the head).
NOTE: Typical values and ranges are provided for some physical contact inputs for illustrative purposes. Specific embodiments adjustable adapted (D14) for a specific situation, input limitations (D3), etc. may have values outside of provided ranges.

TABLE 3

EXAMPLE TRANSDUCERS

| Device | Exemplary Commercially Available Transducer | Example Input Type |
|---|---|---|
| ANALOG TRANSDUCERS | | |
| Piezoelectric sensors | PCB 208C01 | Force |
| | Omega PX271A-020G5V | Force (pressure) |
| | Pyzoflex | Force (pressure), Contact (thermal) |
| | PCB RH240A01 | Strain |
| Integrated electronic piezoelectric (IEPE) accelerometers | Althen AV3145M15 | Motion (e.g. vibration) |
| | Dytran 1051V1 | Force |
| Strain gages | SGD-2/350-DY13 | Force (incl. pressure) |
| Load cells | Omega LCM302-200N | Force (incl. pressure) |
| Linear variable differential transformer (LVDT) linear position sensors | Macro Sensors PR 812 | Displacement |
| Reaction torque sensors | Omega TQM202-1 | Motion (rotation), Force (torque) |
| Potentiometers | CTS series 282 | Motion (rotation) |
| | CTS Series 442 | Displacement |
| Photodiodes | Osram SFH 203 PFA | Contact (optical) |
| Solar cells | IXYS KXOB22-12X1 | Contact (optical) |
| Thermistors | Omega TH-10-44006-1 | Contact (thermal) |
| Thermocouples | Omega HSTC-TT-K-24S-36 | Contact (thermal) |
| Resistance temperature detectors | Omega PR-21A-3-100-A-1 | Contact (thermal) |
| Piezoresistive accelerometer | Endevco 7265A-HS | Motion (acceleration) |
| Force sensing resistors (FSRs) | Sensitronics 1 Inch ThruMode FSR | Force |
| Capacitive touch sensors | Atmel AT42QT1011-TSHR | Contact, Force (incl. pressure), Displacement |
| Surface acoustic wave (SAW) sensor | Senseor SSE E015 | Force (incl. pressure, torque), Displacement, Motion (rotation), Mass |
| | Senseor TSE F143 | Contact (thermal) |
| Hall effect sensors | Analog Devices AD22151G, | various |
| DIGITAL TRANSDUCERS (≥2 bits of resolution) | | |
| Microelectromechanical (MEMS) accelerometers | Analog Devices ADXL375 | Motion |
| Integrated digital temperature | Texas Instruments LM70 | Contact (thermal) |
| | Texas Instruments TMP006 | Contact (thermal) |
| Inductance digital transducers | Texas Instruments LDC1000 | various |
| Hall effect sensors | Honeywell SL353HT | various |
| Ultrasonic distance sensor | Maxbotix MB1003 | Distance, Displacement |
| Lidar/pulsed light | Pulsed Light's LIDAR-Lite | Distance, Displacement |
| MAGNETICALLY-ACTUATED DIGITAL TRANSDUCERS | | |
| Hall effect sensors (digital with 1 bit resolution - as example, digital with ≥2 bit resolution - above, analog - above) | Melexis US1881 | various |
| Variable reluctance speed sensors | Motion Sensors PC51-6E | Motion (rotation) |

TABLE 4

EXAMPLE METHODS OF DATA RETURN FOR DIGITAL TRANSDUCERS

| Return Method | Format | Example Transducer |
|---|---|---|
| Serial peripheral interface (SPI) | Digital protocol | National Instruments LM71 |
| Inter-integrated circuit communications (I2C) | Digital protocol | Texas Instruments LM73 Honeywell HMC5883L |
| Universal asynchronous receiver/transmitter (UART) | Digital protocol | Robot Electronics SRF02 Ultrasonic Rangefinder |
| Universal serial bus (USB) | Digital protocol | National Instruments USB-TC01 |
| 4-20 mA Current Loop | Analog | LM73 with MSP430 microcontroller and DAC161P997 current DAC |

TABLE 5

EXAMPLE INPUT SIGNALS TO VARIOUS DECISION MAKING APPARATUSES

| Input Signal | Type |
|---|---|
| Voltage | Analog |
| Current | Analog |
| Universal asynchronous receiver/transmitter (UART) | Digital protocol |
| Serial peripheral interface (SPI) | Digital protocol, serial |
| Inter-integrated circuit (I2C) | Digital protocol, serial |
| Universal serial bus (USB) | Digital protocol, serial |
| PCI Express bus (PCIe) | Digital protocol, serial |
| Electric Industries Association RS-232 | Digital protocol, serial |
| Peripheral component interconnect | Digital protocol, parallel |
| Industry standard architecture (ISA) | Digital protocol, parallel |
| General purpose interface bus (GPIB) | Digital protocol, parallel |
| Amplitude modulated | Modulated signal |
| Frequency modulated | Modulated signal |
| Phase modulated voltage | Modulated signal |
| Phase modulated current | Modulated signal |
| Phase modulated radio waves | Modulated signal |
| Pulse-width modulated voltage | Modulated signal |
| Pulse-frequency modulated voltage | Modulated signal |

TABLE 6

EXAMPLE MAIN COMPONENTS OF DECISION MAKING APPARATUSES

| Device | Manufacturer |
|---|---|
| MICROCONTROLLERS | |
| MSP430F5529 | Texas Instruments |
| CG8001AA | Cypress |
| AVR 8-bit and 32-bit, ARM-based, 802.15.4 compatible series | Atmel |
| UNO, MICRO, MEGA, Robo, Nano series | Smart Projects, SparkFun, Gravitech |
| EMBEDDED COMPUTERS | |
| V24XX, V26XX series | MOXA |
| COMe, ETX, EPIA, VAB series | Via |
| PXI-XXX, PXIe-XXXX series | National Instruments |
| Various Intel or AMD CPU capable microATX systems | various |
| FIELD PROGRAMMABLE GATE ARRAYS (FPGAS) | |
| Virtex, Spartan, Artix, EasyPath, Kintex series | Xilinx |
| Cyclone, Arria, Stratix series | Altera |
| RIO series | National Instruments |
| AT40K, AT40KAL | Atmel |
| ECP, XP, MACH series | Lattice Semiconductor |

TABLE 6-continued

EXAMPLE MAIN COMPONENTS OF DECISION MAKING APPARATUSES

| Device | Manufacturer |
|---|---|
| COMPLEX PROGRAMMING LOGIC DEVICES (CPLDS) | |
| Coolrunner series, XA9500XL, XC9500XL | Xilinx |
| Max series | Altera |
| ATF 15XX series, F750C, F2500, | Atmel |
| MACH XO, ispMACH 4000 series | Lattice Semiconductor |
| ANALOG CIRCUITS | |
| various circuits known in the art | Custom, Various |

TABLE 7

EXAMPLE PARAMETERS FOR ADJUSTABLE ADAPTATION TO USER INPUT LIMITATION(S)

| Parameter | Type of Parameter | Typically Adjusted By: |
|---|---|---|
| Threshold of derivative of transducer signal | Electrical | Caregiver |
| Threshold of transducer signal level | Electrical | Caregiver |
| Threshold of derivative of transducer signal with respect to time | Electrical | Caregiver |
| Root mean square (RMS) level | Electrical | Caregiver |
| Threshold of the ratio of one transducer to another transducer | Electrical | Caregiver |
| Threshold of derivative of the ratio of one transducer to another transducer with respect to time | Electrical | Caregiver |
| Strength of electromagnet | Electrical | Installer, Algorithm |
| Brightness of variable-intensity light-based proximity sensor | Electrical | Installer, Caregiver, Algorithm |
| Training data | Electrical, Machine Learning | Patient, Caregiver, Installer, Algorithm |
| Weights (machine learning) | Electrical, Machine Learning | Algorithm |
| Branch metric threshold | Electrical, Machine Learning | Patient, Caregiver, Installer, Algorithm |
| Fixed pre-load to force or displacement sensor | Mechanical | Installer, Manufacturer |
| Variable pre-load to strain gauge mount | Mechanical | Caregiver, Patient |
| Displacement of button or grip housing | Mechanical | Any user |
| Variable activation pressure | Mechanical | Any user |
| Stiffness of activation mechanism | Mechanical | Installer, Manufacturer |
| Temperature sensor distance from contact point | Mechanical | Caregiver |
| Strength of permanent magnet | Mechanical | Manufacturer, Installer |
| Color or inherent intensity of bulb, LED, etc. | Mechanical | Manufacturer |
| Wavelength range of speaker or signal generator | Mechanical | Manufacturer |
| Opacity of light-based proximity sensor | Mechanical | Manufacturer |

TABLE 8

EXAMPLE CONTROL SIGNALS

| Example Control Signal(s) | Signal Type | Possible Controlled Apparatus(es) |
|---|---|---|
| Unsynchronized parallel signal lines | Electrical: Static Digital Signal | Nurse call system, Hospital Bed such as Invacare Full (control based on voltage, current, or impedance) | 
| | | Electric Bed (ID: 5410IVC), Motorized Trendelenburg chair or bed, Motorized gurney or birthing bed |
| SPI | Electrical: Digital Protocol | Touch screen, Video game |
| I2C | Electrical: Digital Protocol | LCD display, Keypad |
| USB | Electrical: Digital Protocol | Computer, Cell phone, Electronic picture frame, Mouse, MOBI2, Speech synthesizer |
| UART | Electrical: Digital Protocol | Speech synthesizer, Text display device |
| RS-232 | Electrical: Digital Protocol | Modem, Speech synthesizer, Text display device, Printer |
| Telecommunications Industry Association/ Electronic Industries Alliance RS-485 | Electrical: Digital Protocol | Text display device, Security system |
| 4-20 mA or 10-50 mA current loop control lines | Electrical: Analog | Radio, Telephone, |
| Infrared remote control protocols | Electrical: Analog, Infrared protocol | Vehicle door/lock, Door lock, Motorized window, Motorized blinds, Television, Lighting, Lamps |
| Infrared Data Association (IrDA) protcols | Electrical: Analog, Infrared protocol | Medical devices, Computers, |
| Bluetooth | Electrical: Wireless protocol | Printer, Tablet, Cell phone, Insulin pump, Elevator |
| 802.15.4 | Electrical: Wireless protocol | Garage door opener, Thermostat, Telephone |
| 802.11 | Electrical: Wireless protocol | Computer, Camera, Smartphone, Tablet (e.g. iPad, Nook, Kindle), Printer |
| Proprietary wireless protocols | Electrical: Wireless protocol | Hospital bed control, Clock, Fan |
| Rotation of a knob | Mechanical | Radio, CD/DVD player, Thermostat |
| Pressing/releasing physical button(s) | Mechanical | Bed control, Alarm clock, Help request/alarm |
| Linear displacement of a control rod | Mechanical | Window curtains and blinds, Sliding door |

TABLE 9

IMPLEMENTATIONS OF EXAMPLE 1

| Element or Feature | Particular Embodiment of Element or Feature |
|---|---|
| Input limitation | ALS induced: Severely reduced strength, dexterity, & motor control, particularly in hands Hand tremors Complete voice loss |
| Intended command | Commands to bed (lift/lower head, feet, bed) Yes/No communication |
| Physical contact input | Hand squeeze |
| Adjustable adaptation | Adapt activation of grip units to hand tremors and hand grip strength |
| Adjustable adaptation parameter(s) | See TABLE 10 |

TABLE 9-continued

IMPLEMENTATIONS OF EXAMPLE 1

| Element or Feature | Particular Embodiment of Element or Feature |
|---|---|
| Transducing apparatus | Two grip-activated pendants (one per hand) with corresponding circuitry & components (partially listed below) Transducer mechanical apparatuses (grip housings) 3D printed for advantageous activation by user, geometry chosen by combining geometrical elements of multiple common objects selected by user and caregivers |
| Digital transducers with ≥2 bit resolution | None |
| Analog sensors | Strain gage - Omega ¼ bridge 350Ω (SGD-7/350-LY11) |
| Magnetically-activated digital transducers | None |
| Electrical signal | Analog voltage strain gage transducer output, See Table 3 10 bit ADC code (ARDUINO EMBODIMENT) 24 bit ADC code (cRIO EMBODIMENT) |
| Decision-making apparatus - & - Signal generator (combined in these implementations) | ARDUINO EMBODIMENT Instrumentation Amplifier - INA826AID from Texas Instruments Potentiometer - TC33X-2-104E from Bourns Microcontroller - Arduino Uno integrated micro-controller and peripherals (diagrammed in FIG. 8) Solid State Relays - AQY282S from Panasonic LCD Display - 20-011-913-A03 from SainSmart Custom Arduino code (APPENDIX 1) cRIO EMBODIMENT Strain Gage Input Module - NI 9237 Current Output Module - NI 9265 (to excite the buzzer for haptic feedback) Solid State Relay Switch Module - NI 9481 FPGA backplane - NI cR10-9113 Real Time Controller - NI cR10-9024 Custom LabVIEW code |
| Transmittance apparatus | Cable(s) to hospital bed controller connector Cable(s)/wire(s) to feedback mechanism |

APPENDIX 1

CUSTOM ARDUINO CODE OF AN IMPLEMENTATION OF AN EMBODIMENT OF EXAMPLE 1.

```
[1]  #include <Wire.h>
[2]  #include <LiquidCrystal_I2C.h>
[3]  #include <EEPROM.h>
[4]
[5]  //-----------------------------------------------------------
[6]  // LCD Setup
[7]  //-----------------------------------------------------------
[8]  //Define the I2C to Parallel pin assignments
[9]  //These are part of the LCD module, not Arduino pins
[10] #define BACKLIGHT_PIN   3
[11] #define En_pin          2
[12] #define Rw_pin          1
[13] #define Rs_pin          0
[14] #define D4_pin          4
[15] #define D5_pin          5
[16] #define D6_pin          6
[17] #define D7_pin          7
[18] LiquidCrystal_I2C
     lcd(0x3F,En_pin,Rw_pin,Rs_pin,D4_pin,D5_pin,D6_pin,D7_pin);
     //configure the
     LCD to be called "lcd" and found at it's I2C address
[19]
[20] //-----------------------------------------------------------
[21] // Pin Assignments
[22] //-----------------------------------------------------------
[23] //   Pin      Pin Relay   Function
[24] //    1          K1       Head Up
[25] //    3          K2       Head Down
[26] //    4          K3       Feet Up
[27] //    6          K4       Feet Down
[28] //    8          K5       Doorbell
[29] const int relays[ ]={1,3,4,6,8};
[30] const int MAX_STATE = 4; //RBG: you must handcode
     MAX_STATE to be the index of the last relay[ ] state
[31] // Threshold buttons
[32] // Select: low = Threshold 1 selected, high = Threshold 2 selected
[33] const int Thresh_select_pin=12;
[34] const int Thresh_down_pin=A2;
```

TABLE 10

EXAMPLE PARAMETERS OF EXAMPLE 1

| Figure Indicia | Parameter Type: Description [units] | Typical Adjuster | Example Adjustment Method | Typical Value | Typical Range |
|---|---|---|---|---|---|
| 304 | Mech/Elect: Activation force by power grip of hand (via displacement, elastic modulus, preload, thresholds, etc) [N] | Manufacturer, Installer, Caregiver | Varies | 5-20 | 0.5-200 |
| 302, 306/ 701-2 | Mechanical: Pre-activation separation of hand grip housing halves [mm] | Installer, Caregiver | Threaded boss | 10 | 0.01-80 |
| | Alternatively - - - | Installer | Shimming | — | — |
| 303 | Mechanical: Elastic modulus of flexible beam [GPa] | Manufacturer, Installer | Selection of material | 69 | 0.01-400 |
| 303-4 | Mechanical: Strain-gauge preload, as radius of curvature of flexible beam [m] | Manufacturer, Installer | Preparation of material | 1 | 0-100 |
| | Alternatively - - - | Caregiver | Threaded boss | 1 | 0-100 |
| 906 | Electrical: Resistance of half-bridge (e.g. potentiometer) [kΩ] | Caregiver, User | Knob | 1 | 0.120-20 |
| 803-6 | Electrical: Push-button-controlled pullup resistors as threshold for invidual grips [kΩ] | Caregiver | Buttons | 10 | 1-100 |
| 910 | Electrical: Gain [n/a] | Caregiver | Knob, Slider | 20 | 1-1000 |

APPENDIX 1-continued

CUSTOM ARDUINO CODE OF AN IMPLEMENTATION OF
AN EMBODIMENT OF EXAMPLE 1.

```
[35]   const int Thresh_up_pin=A3;
[36]   // Buzzer is two pins shorted together to get more drive current for
       this rev
[37]   const int Buzzer[ ]={10,11};
[38]
[39]   //-------------------------------------------------------------------
           ----
[40]   // Global Variables
[41]   //-------------------------------------------------------------------
           ----
[42]   int LCD_clear_count=0; //used to clear the LCD screen periodically
[43]   int Threshold1=50, Threshold2=50; // will need to read these from the
       EEPROM later
[44]   int ADC1_code, ADC2_code; //These are the variables to store the
       ADC readings
[45]   int Grip1_reading, Grip2_reading; //These are the scaled readings
[46]   boolean Thresh1_up, Thresh1_down, Thresh2_up, Thresh2_down;
       //These are the button press digital inputs, '0' represents a push
[47]   boolean Thresh1_up_prior=0, Thresh1_down_prior=0,
       Thresh2_up_prior=0, Thresh2_down_prior=0; //These are a
       recall of the last state of the digital inputs, used to count each
       press as only one event
[48]   //int Thresh1_up_pin=13, Thresh1_down_pin=12,
       Thresh2_up_pin=11, Thresh2_down_pin=10; //These are the pin
       numbers used for the buttons
[49]   //int Output0=9, Output1=8, Output2=7, Output3=6, Output4=5;
       //These are the pins that output to relays or other actuators
[50]   boolean Grip1_active=0, Grip2_active=0; //These indicate that
       the grip has exceeded its threshold
[51]   boolean Grip1_active_prior=1, Grip2_active_prior=1; //These
       recall the last state of the grip, used for detecting threshold crossing
       as a single event
[52]   int Active_mode=0;
[53]
[54]
[55]   //-------------------------------------------------------------------
           ----
[56]   // Setup
[57]   //-------------------------------------------------------------------
           ----
[58]   void setup( )
[59]   {
[60]       //Setup the LCD
[61]       lcd.setBacklightPin(BACKLIGHT_PIN,POSITIVE);
[62]       lcd.setBacklight(HIGH);
[63]       lcd.begin(20,4);
[64]       lcd.home ( );
[66]       lcd.print(" Grip1:   ");
[66]       lcd.setCursor ( 0, 1 );
[67]       lcd.print("Thrshld1: ");
[68]       lcd.setCursor ( 0, 2 );
[69]       lcd.print(" Grip2:   ");
[70]       lcd.setCursor ( 0, 3 );
[71]       lcd.print("Thrshld2: ");
[72]
[73]       //Initialize input buttons
[74]       pinMode(Thresh_select_pin,INPUT);
[75]       pinMode(Thresh_down_pin,INPUT);
[76]       pinMode(Thresh_up_pin,INPUT);
[77]       digitalWrite(Thresh_select_pin,HIGH);
[78]       digitalWrite(Thresh_down_pin,HIGH);
[79]       digitalWrite(Thresh_up_pin,HIGH);
[80]       //Initialize all relays to OFF
[81]       for(int i=0;i< sizeof(relays);i++) {
[82]          digitalWrite(relays[i], 1);
[83]          pinMode(relays[i], OUTPUT);
[84]       }
[85]       //Initialize all buzzer pins to OFF
[86]       digitalWrite(Buzzer[0], 1);
[87]       digitalWrite(Buzzer[1], 1);
[88]       pinMode(Buzzer[0],OUTPUT);
[89]       pinMode(Buzzer[1],OUTPUT);
[90]       //Use the external reference provided by 3.3V_AUX
[91]       analogReference(EXTERNAL);
[92]       //Retrieve the thresholds from the EEPROM
[93]       Threshold1=EEPROM.read(0);
[94]       Threshold2=EEPROM.read(1);
```

APPENDIX 1-continued

CUSTOM ARDUINO CODE OF AN IMPLEMENTATION OF
AN EMBODIMENT OF EXAMPLE 1.

```
[95]    Threshold1=20; //TODO: REOMVE THESE DEBUG LINES
[96]    Threshold2=35;
[97]    //The first time the microcontroller is loaded it will have 255 stored
        in the EEPROM for all unwritten values
[98]    //This 'if' will therefore initialize the thresholds to midscale
[99]    if(Threshold1>100 && Threshold2>100) {
[100]       Threshold1=50;
[101]       Threshold2=50;
[102]    }
[103] }
[104]
[105]
[106] //-------------------------------------------------------------------
          ----
[107] // Loop
[108] //-------------------------------------------------------------------
          ----
[109] void loop( )
[110] {
[111]     ADC1_code=analogRead(A0); //Read the grip inputs
[112]     ADC2_code=analogRead(A1);
[113]     Grip1_reading=ADC1_code/10.23; //Scale the grip
       inputs to 0-100%
[114]     Grip2_reading=ADC2_code/10.23;
[115]     Grip1_active=(Grip1_reading > Threshold1); //Determine
       whether the grip readings exceed the thresholds
[116]     Grip2_active=(Grip2_reading > Threshold2);
[117]
[118]     //RBG: re-initialize the select pin just to make sure it's in the
       right state. we shouldn't really need to do this!!
[119]     //Read the threshold buttons
[120]     Thresh1_up=0;
[121]     Thresh1_down=0;
[122]     Thresh2=0;
[123]     Thresh2_down=0;
[124]     if(digitalRead(Thresh_select_pin)) {
[125]         Thresh1_up=digitalRead(Thresh_up_pin);
[126]         Thresh1_down=digitalRead(Thresh_down_pin);
[127]     } else {
[128]         Thresh2_up=digitalRead(Thresh_up_pin);
[129]         Thresh2_down=digitalRead(Thresh_down_pin);
[130]     }
[131]
[132]
[133]     // up = A3, down = A2, select = 12
[134]     lcd.setCursor(0,0);
[135]     lcd.print(digitalRead(Thresh_select_pin)); lcd.print(" <-sel ");
[136]     lcd.setCursor(0,1) ;
[137]     lcd.print(digitalRead(Thresh_up_pin)); lcd.print(" <-up ");
[138]     lcd.setCursor(0,2);
[139]     lcd.print(digitalRead(Thresh_down_pin));
      lcd.print(" <-down ");
[140]
[141]
[142]
[143]     //Print the grip readings and thresholds to the LCD
[144]     lcd.setCursor(10,0);
[145]     lcd.print(Grip1_reading); lcd.print(" "); //print blank spaces
       to erase previously written zeroes
[146]     lcd.setCursor(10,2);
[147]     lcd.print(Grip2_reading); lcd.print(" "); //print blank spaces
       to erase previously written zeroes
[148]     lcd.setCursor(10,1);
[149]     lcd.print(Threshold1); lcd.print(" "); //print blank spaces to
       erase previously written zeroes
[150]     lcd.setCursor(10,3);
[151]     lcd.print(Threshold2); lcd.print(" "); //print blank spaces to
       erase previously written zeroes
[152]
[153]
[154]     //Print the buttons readings to the LCD
[155]     /*
[156]     lcd.setCursor(18,0);
[157]     lcd.print(Thresh1_up);
[158]     lcd.setCursor(18,1);
[159]     lcd.print(Thresh1_down);
[160]     lcd.setCursor(18,2);
```

APPENDIX 1-continued

CUSTOM ARDUINO CODE OF AN IMPLEMENTATION OF AN EMBODIMENT OF EXAMPLE 1.

```
[161]     lcd.print(Thresh2_up);
[162]     lcd.setCursor(18,3);
[163]     lcd.print(Thresh2_down);*/
[164]
[165]     if((!Thresh1_up)||(!Thresh1_down)||(!Thresh2_up)||(!Thresh2_down))
          //This checks to see if any buttons have been pressed
[166]     {
[167]        if(Thresh1_up_prior && Thresh1_down_prior &&
          Thresh2_up_prior && Thresh2_down_prior)//Were any of the
          buttons pushed last iteration?
[168]        {
[169]           //Which button was pressed?
[170]           if(!Thresh1_up) {
[171]              Threshold1++;
[172]              EEPROM.write(0,Threshold1);}
[173]           else if (!Thresh1_down) {
[174]              Threshold1--;
[175]              EEPROM.write(0,Threshold1);}
[176]           else if(!Thresh2_up) {
[177]              Threshold2++;
[178]              EEPROM.write(1,Threshold2);}
[179]           else if(!Thresh2_down) {
[180]              Threshold2--;
[181]              EEPROM.write(1,Threshold2);}
[182]
[183]           //coerce threshold values to the range of 0-100
[184]           if(Threshold1>100) Threshold1=100;
[185]           if(Threshold1<0)   Threshold1=0;
[186]           if(Threshold2>100) Threshold2=100;
[187]           if(Threshold2<0)   Threshold2=0;
[188]        }
[189]     }
[190]
[191]     //Store the button states so that we have a memory of whether
          they were pressed or not
[192]     Thresh1_up_prior=Thresh1_up;
[193]     Thresh1_down_prior=Thresh1_down;
[194]     Thresh2_up_prior=Thresh2_up;
[195]     Thresh2_down_prior=Thresh2_down;
[196]
[197]     //Activate appropriate outputs if Grip1 is active
[198]     //Set a soft copy of relay states and set them all to OFF
[199] //     int nextRelayStates [sizeof(relays)];
[200] //     for(int i=0;i<sizeof(nextRelayStates);i++)
[201]     int nextRelayStates [5];
[202]     for(int i=0;i<5;i++)
[203]        nextRelayStates[i]=1;
[204]     if(Grip1_active)
[205]     {
[206]        //Mark the appropriate relay soft copy to ON
[207]        if(Active_mode < sizeof(relays))
[208]           nextRelayStates[Active_mode]=0;
[209]        //Display that the output is activated
[210]        lcd.setCursor(14,0);
[211]        lcd.print("ACTIVE");
[212]     }
[213]     else //deactivate outputs if Grip1 is not active
[214]     {
[215]        //Display that the output is not activated
[216]        lcd.setCursor(14,0);
[217]        lcd.print("      ");
[218]     }
[219]     //Apply the relay states from the soft copy
[220] //     for(int i=0;i<sizeof(nextRelayStates);i++)
[221]     for(int i=0;i<5;i++)
[222]        digitalWrite(relays[i],nextRelayStates[i]);
[223]
[224]     //Change modes if Grip2 trigger event occurs
[225]     if(Grip2_active && !Grip2_active_prior)
[226]     {
[227]        //Handle rollovers
[228]        if(Active_mode == MAX_STATE)
[229]           Active_mode = 0;
[230]        else
[231]           Active_mode++;
[232]        //Activate the Buzzer
[233]        for(int i = 0; i <Active_mode + 1; i++)
[234]        {
[235]           digitalWrite(Buzzer[0],0);
[236]           digitalWrite(Buzzer[1],0);
[237]           lcd.setCursor(15,3);
[238]           lcd.print("BUZZ");
[239]           delay(300)
[240]           digitalWrite(Buzzer[0],1);
[241]           digitalWrite(Buzzer[1],1);
[242]           lcd.setCursor(15,3);
[243]           lcd.print("    ");
[244]           delay(100);
[245]        }
[246]     }
[247]     //Print the current state
[248]     lcd.setCursor(14,2);
[249]     lcd.print("State"); lcd.print(Active_mode);
[250]
[251]     //Store the last state of the Grips
[252]     Grip1_active_prior = Grip1_active;
[253]     Grip2_active_prior = Grip2_active;
[254] }
```

We claim:

1. An accessibility apparatus, which is a control apparatus for engaging and actuating particular powered functions of anatomical support apparatus and auxiliary apparatus and is configured suitably for use by at least one patient having muscular or neural limitations that cause input limitations for the patient, the entire body or portions thereof of said patient being positioned and supported in a preferred configuration for treatment of said patient or in an optimal orientation for comfort or health for said patient, said input limitations of said patient including at least one input limitation selected from the group consisting of: limited muscle control, limited dexterity, and limited strength, said control apparatus adjustably adapted to at least one input limitation of said patient, in which said control apparatus:
(i) determines at least one intended command of said patient from a physical contact input applied by said patient to some portion of a transducer mechanical assembly of said control apparatus, and
(ii) generates at least one control signal therefrom for controlling at least one controlled apparatus of said anatomical support apparatus and/or said auxiliary apparatus;

the adjustable adaptation to said at least one input limitation of said patient other than solely comprised of:
(i) geometry, orientation, or arrangement of input structures,
(ii) timing or sequence of inputs, or
(iii) any combination thereof;

said physical contact input other than a voice signal and other than an exclusively electrical phenomenon generated by brain tissue;

said physical contact input transduced otherwise than solely by:
(i) non-contact tracking of the motion of an eyeball,
(ii) optical transducers not requiring physical contact with some portion of said transducer mechanical assembly,
(iii) sip-and-puff apparatus,
(iv) touch-responsive screens lacking adjustable adaptation parameters to adjust response by said control apparatus to said at least one input limitation of said patient, or (v) any combination thereof;
said control apparatus comprising:
(a) a transducing apparatus configured to transduce said physical contact input of said patient operating under said input limitations, said physical contact input representing said at least one intended command of said patient to said controlled apparatus, said transducing apparatus containing transducers, wherein at least one of said transducers is selected from the group consisting of:
(i) digital transducers of at least two (2) bits of resolution,
(ii) analog sensors and
(iii) magnetically activated digital transducers, and
said transducing apparatus further configured to generate from said physical contact input at least one electrical signal;
(b) a decision making apparatus wherein said transducing apparatus and said decision making apparatus is adjustably adapted via at least one adjustable adaptation parameter such that said decision making apparatus determines said at least one intended command of said patient from said electrical signal,
(c) at least one signal generator, wherein said decision making apparatus is further configured to direct said signal generator to generate said control signal sufficient to direct said controlled apparatus to effect said intended command; and
(d) a transmittance apparatus configured to convey said control signal to said controlled apparatus such that it effects said at least one intended command of said patient;
wherein:
a) said transducing apparatus is comprised of first and second hand-held pendants configured to at least transduce grip intensities of said patient on at least one of said pendants into at least one electrical signal corresponding to an applied intensity, wherein at least one of said first and second hand-held pendants comprises a first housing and second housing joined along at least one end or side, said first and second housing configured such that at least some portion of said first housing is separated from at least some portion of said second housing such that said portion of said first housing moves or deforms relative to said portion of said second housing upon application of said grip intensities,
b) said decision making apparatus is configured (1) to advance from a current state to one of a plurality of available states upon an adjustably predetermined first grip intensity being one of said grip intensities and being applied to said first hand-held pendant, and (2) to activate a new current state upon an adjustably predetermined second grip intensity being one of said grip intensities and being applied to said second hand-held pendant, and
c) adjustability of the grip intensity required for activation of either of said pendants is comprised of the at least one said adjustable adaptation parameter,
whereby said control apparatus enables said patient to control at least one predetermined function of said controlled apparatus by applying said first grip intensity to said first hand-held pendant to induce said decision making apparatus to advance said current state of control apparatus through said available states until said new current state is a desired state for said patient, said desired state being subsequently activated by said patient applying said second grip intensity to said second hand-held pendant, and said desired state remaining activated until said patient ceases applying said second grip intensity (D19).

2. A control apparatus configured suitably to enable a person having two hands capable of gripping, but suffering from neural or muscular limitation of physical contact inputs (PCI), to control at least one device, said control apparatus comprising:
(a) a transducing apparatus (TA) configured to transduce a plurality of PCI of said person suffering from at least one input limitation comprising limited:
muscle control (MC), dexterity (D), or strength (S);
said PCI comprising grip intensities and representing a plurality of intended commands (IC) of said person to at least one controlled apparatus (CA);
said TA comprising a first and second grip unit configured suitably to be received in a first and second hand of said person, and disposed accessible thereto, and each configured to be activated by an adjustably predetermined grip intensity, and to generate therefrom at least one electrical signal;
at least one said first and second grip unit comprising a first housing and second housing joined along at least one end or side, said first and second housing configured such that at least some portion of said first housing is separated from at least some portion of said second housing such that said portion of first housing moves or deforms relative to said portion of second housing;
(b) a decision making apparatus (DMA) configured to receive said electrical signal, and further configured to determine therefrom a current said IC, wherein said DMA is configured to cycle through a plurality of states in a state machine upon a first appropriate grip intensity (AGI) being applied to said first grip unit;
said states representing functions available for activation, and said DMA being further configured to activate a current state upon a second AGI being applied to said second grip unit, thereby activating a represented function corresponding to the current state;
said DMA configured to determine said first and second AGI regardless of variations therein and corresponding variations in the at least one electrical signal generated therefrom, said DMA being adjustably adapted to accommodate changes in said input limitation via at least one first adjustable adaptation parameter (AAP) selected from the group comprising:
thresholds, filters, and any combination thereof;
(c) at least one signal generator, directed by said DMA to generate at least one control signal; and
(d) a transmittance apparatus configured to convey said control signal to said CA, such that it effects said IC of said person toward said device.

3. The control apparatus of claim 2 wherein said at least one of said first and second grip unit further comprises:
(a) a flexible element disposed between said first and second housings and configured to deflect proportionately to a grip intensity urging said portion of first housing and said portion of second housing together; and
(b) at least one sensor configured to detect said movement or deformation.

4. The control apparatus of claim 3 wherein:
(a) a pressing element is contained in said first housing;
(b) said flexible element comprises a beam approximately as long as, and entirely enclosed between the outer perimeter of, said first and second housings, said beam being configured as a strip substantially wider than the thickness thereof and fixed sufficiently securely relative to one of said first and second housings, and end or center of said beam being configured to be sufficiently free to bend when deflected by said pressing element;

(c) said sensor is mounted to said beam and configured to detect deflection thereof; and (d) said at least one grip unit is provided with at least one second AAP, varied to accommodate changes in said input limitation, selected from the group comprising: (i) extent of said separation between said portion of first housing and said portion of second housing, (ii) spring strength maintaining said separation, and (iii) any combination thereof.

5. The control apparatus of claim 4 wherein:

(a) said first and second grip units are configured to be substantially sealed;

(b) said sensor is a strain gage in a quarter-bridge, half-bridge, or full-bridge configuration; and (c) resistance of said strain gage varies in proportion to deflection of said beam upon application of a grip intensity, in the range between 0 and 1,100 Newtons, to said at least one grip unit.

6. The control apparatus of claim 5 configured as a system with at least one feedback apparatus configured to provide feedback selected from the group comprising:

(a) audible feedback by a speaker or buzzer, (b) visible feedback by a light source or text or image display, (c) haptic feedback by a vibrating mechanism, and (d) any combination thereof;

said feedback apparatus configured to indicate to said person a change of said current state of said state machine to a new current state upon application of said AGI to said first grip unit.

7. The control apparatus of claim 5 wherein:

(a) said input limitation comprises tremors or shakes; and (b) said DMA further comprises a control logic element and is configured as a signal processing system comprising a low-pass filter comprising an infinite impulse response filter or finite impulse response filter with a filter frequency adaptably adjusted to reject tremors or shakes.

8. The control apparatus of claim 5 wherein:

(a) said input limitation comprises high-baseline grip force; and (b) said DMA is provided with at least one third AAP, adaptably adjusted to nullify muscle tension causing said high-baseline grip force, said third AAP comprising at least one of: (i) grip strength threshold, (ii) sensor hysteresis, and (iii) any combination thereof.

9. The control apparatus of claim 5 wherein said at least one CA comprises a patient support apparatus and an alarm device or assistance-call system.

10. The control apparatus of claim 3 wherein:

(a) said DMA further comprises at least one processor;

(b) said DMA is configured to determine said IC by determining an intended grip force from a grip intensity applied by said person, said DMA being configured to effect adjustment of at least said first AAP on a continuing basis, corresponding to continual changes in said input limitation, according to a dimensionality reduction method performed by said processor on data from a plurality of sensors; and (c) said plurality of sensors comprises at least one of:

(i) a plurality of sensors disposed within at least one of said first or second grip unit, and configured to measure at least one of: (A) grip intensity applied by individual fingers, (B) grip intensity applied by an ulnar side of a hand of said person relative to a radial side of said hand, (C) absolute grip intensity applied by at least one particular portion of a hand of said person, (D) grip intensity applied by at least one particular portion of a hand of said person relative to at least one other particular portion of said hand, and (E) any combination thereof;

(ii) at least one sensor from each of said first and second grip unit, having corresponding functions in each grip unit, and enabling said processor to adjust at least said first AAP of at least one of said first and second grip unit according to a steady grip force applied to the other grip unit, thereby determining said intended grip force regardless of said steady grip force resulting from whole body tension due to limited MC; and (iii) any combination thereof.

11. The control apparatus of claim 3 wherein:

(a) said DMA further comprises at least one processor configured to analyze past electrical signals from said TA, or values derived therefrom, with a classifier algorithm;

(b) said DMA is further configured to determine therefrom an appropriate value, for determining an intent of said person to change or activate said current state, of at least said first AAP of at least one of said first and second grip unit;

(c) said past electrical signals or values derived therefrom are gathered during at least one of: (i) an introductory patient learning session, (ii) a caregiver-initiated learning session, (iii) a recurring or periodic learning session, and (iv) any combination thereof; and (d) said past electrical signals or values derived therefrom are correlated to at least one known IC.

12. The control apparatus of claim 3 wherein said control apparatus is configured for use by a plurality of users:

(a) said DMA being further configured to store a plurality of data sets, each of said data sets associated with one user and comprising:

(i) user identity data and (ii) values of said first AAP; and (b) said DMA being further configured to set current values of said first AAP according to user identity data of a particular user;

thereby allowing said control apparatus to be more rapidly adapted to said input limitation of said particular user.

13. A system configured for use in a multi-patient treatment, care, or assistance facility, comprising the control apparatus of claim 12 and:

(a) said system being provided with a plurality of grip-sets comprising said first and second grip unit, (b) some portion of said DMA, responsible for managing user parameters, being connected to each of said plurality of grip-sets and comprising at least a central storage and processing unit configured to store said data sets and to set current values of said first AAP of any particular grip-set according to user identity data of said particular user, said particular grip-set being chosen from said plurality of grip-sets.

14. A control apparatus configured suitably to enable a person having at least one hand capable of gripping, but suffering from neural or muscular limitation of physical contact inputs, to control at least one device, said control apparatus comprising:

(a) a transducing apparatus (TA) configured to transduce at least one physical contact input (PCI) of said person suffering from at least one input limitation comprising limited:
(i) muscle control, (ii) dexterity, or (iii) strength;
said PCI comprising a grip intensity representing at least one intended command (IC) of said person to at least one controlled apparatus (CA), said IC being an intent to activate at least one function of said CA;
said TA comprising a grip unit configured suitably to be at least partially received in said hand of said person, and disposed accessible thereto, said grip unit comprising a first housing and second housing joined along at least one end or side, said first and second housing configured such that at least some portion of said first housing is separated from at least some portion of said second housing such that said portion of said first housing moves or deforms relative to said portion of said second housing upon application of said grip intensity;
said grip unit further comprising at least one analog force sensor comprising a force sensitive resistor or strain gage, said grip unit configured to be activated by an adjustably predetermined grip intensity, and to generate therefrom at least one electrical signal;
said grip intensity comprising:
  (i) a pinch grip with strength between 0 and 200 Newtons, and pressing said grip unit between a thumb of said hand and a portion of said hand or between a digit of said hand and a sufficiently firm object, or
  (ii) a grip, on a sufficiently firm object, with strength between 0 and 1,100 Newtons;
(b) a decision making apparatus (DMA) configured to receive said electrical signal, and further configured to determine therefrom said IC, wherein said DMA is configured to activate said at least one function upon an appropriate grip intensity being applied to said grip unit;
said DMA further configured to determine said appropriate grip intensity regardless of variations therein and corresponding variations in the at least one electrical signal generated therefrom, said DMA being adjustably adapted to accommodate changes in said input limitation via at least one first adjustable adaptation parameter (AAP) selected from the group comprising:
thresholds, filters, and any combination thereof;
  (c) at least one signal generator, directed by said DMA to generate at least one control signal; and
  (d) a transmittance apparatus configured to convey said control signal to said CA, such that it effects said IC of said person.

* * * * *

UNITED STATES PATENT AND TRADEMARK OFFICE
CERTIFICATE OF CORRECTION

PATENT NO.         : 9,625,884 B1
APPLICATION NO.    : 14/253866
DATED              : April 18, 2017
INVENTOR(S)        : Ousley et al.

Figure 3:
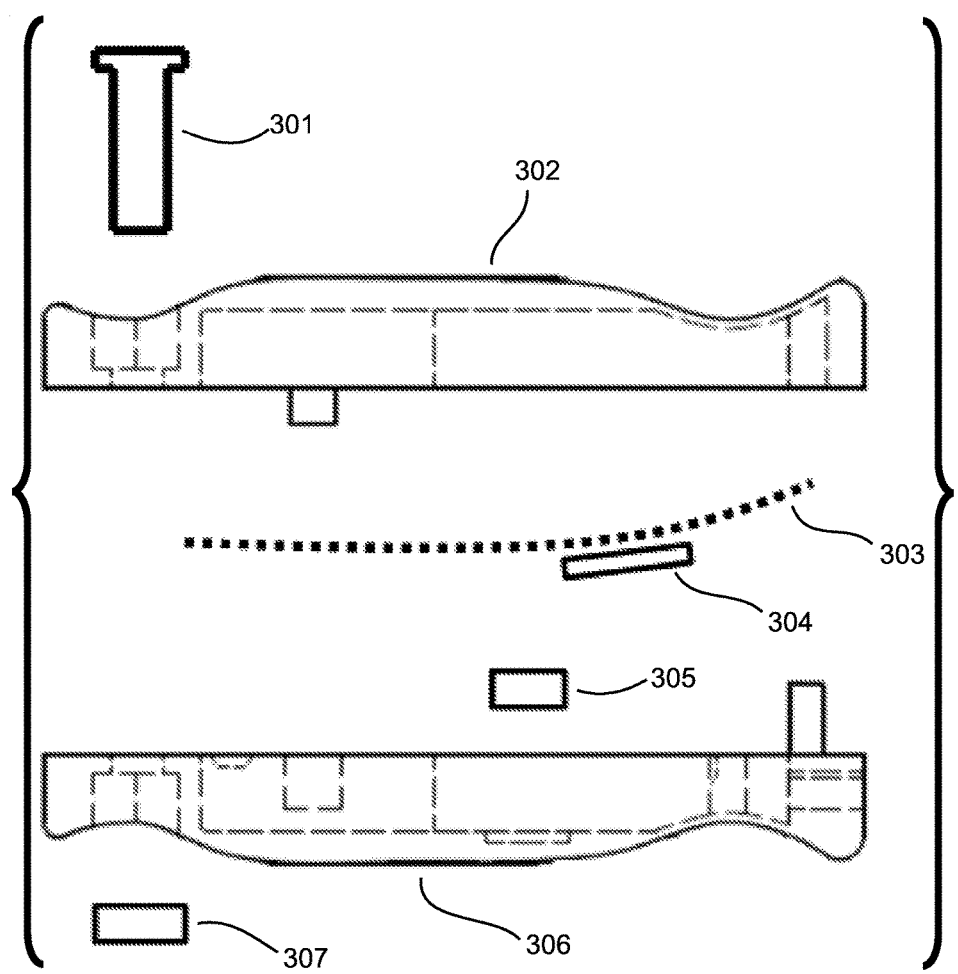
FIG. 3 is an exploded view of one portion of the transducing apparatus in a grip-sensing embodiment.
Figure 4:
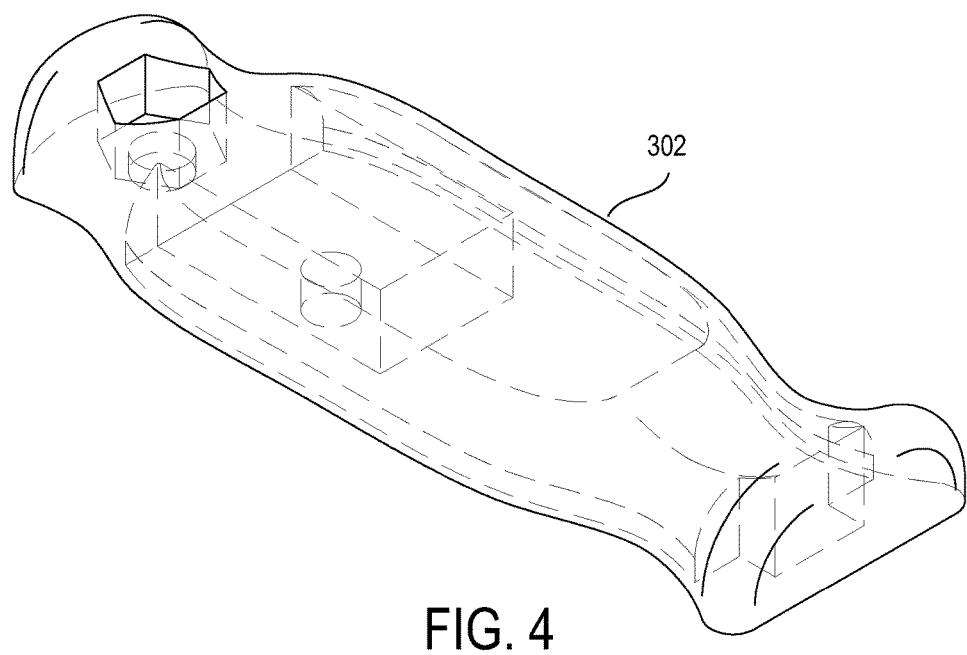
FIG. 4 is an isometric view of a first mating half of a transducer housing assembly of a grip-sensing embodiment.
Figure 5:
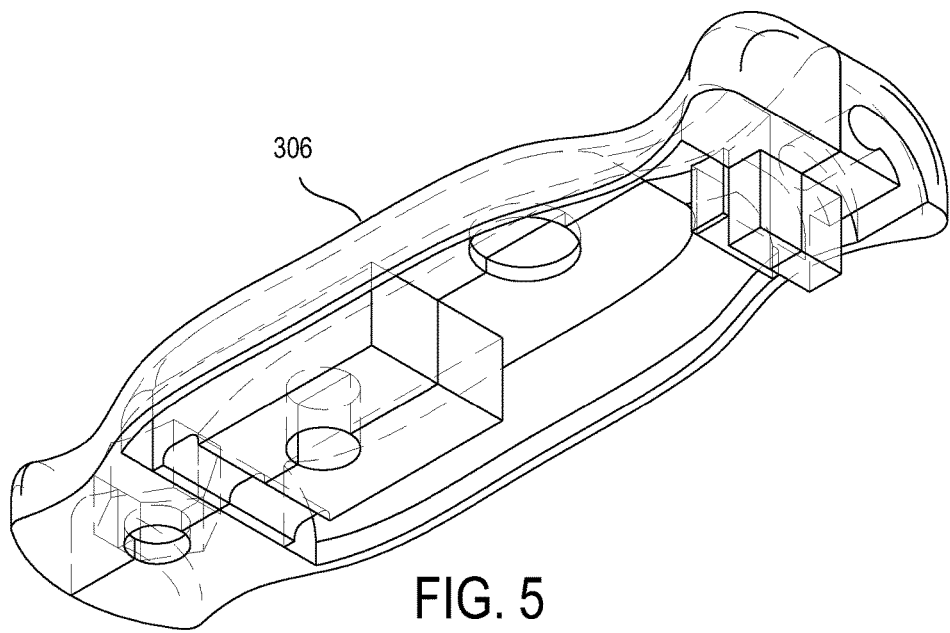
FIG. 5 is an isometric view of a second mating half of a transducer housing assembly of a grip-sensing embodiment.

It is certified that error appears in the above-identified patent and that said Letters Patent is hereby corrected as shown below:

FIG. 3, the boss, which is a pressing element, and protrudes upwards from the right of the top plane of bottom housing shell 306, is referenced in the description as "308" and should be marked in the drawing as reference numeral --308-- with associated lead line.

Figure 6:
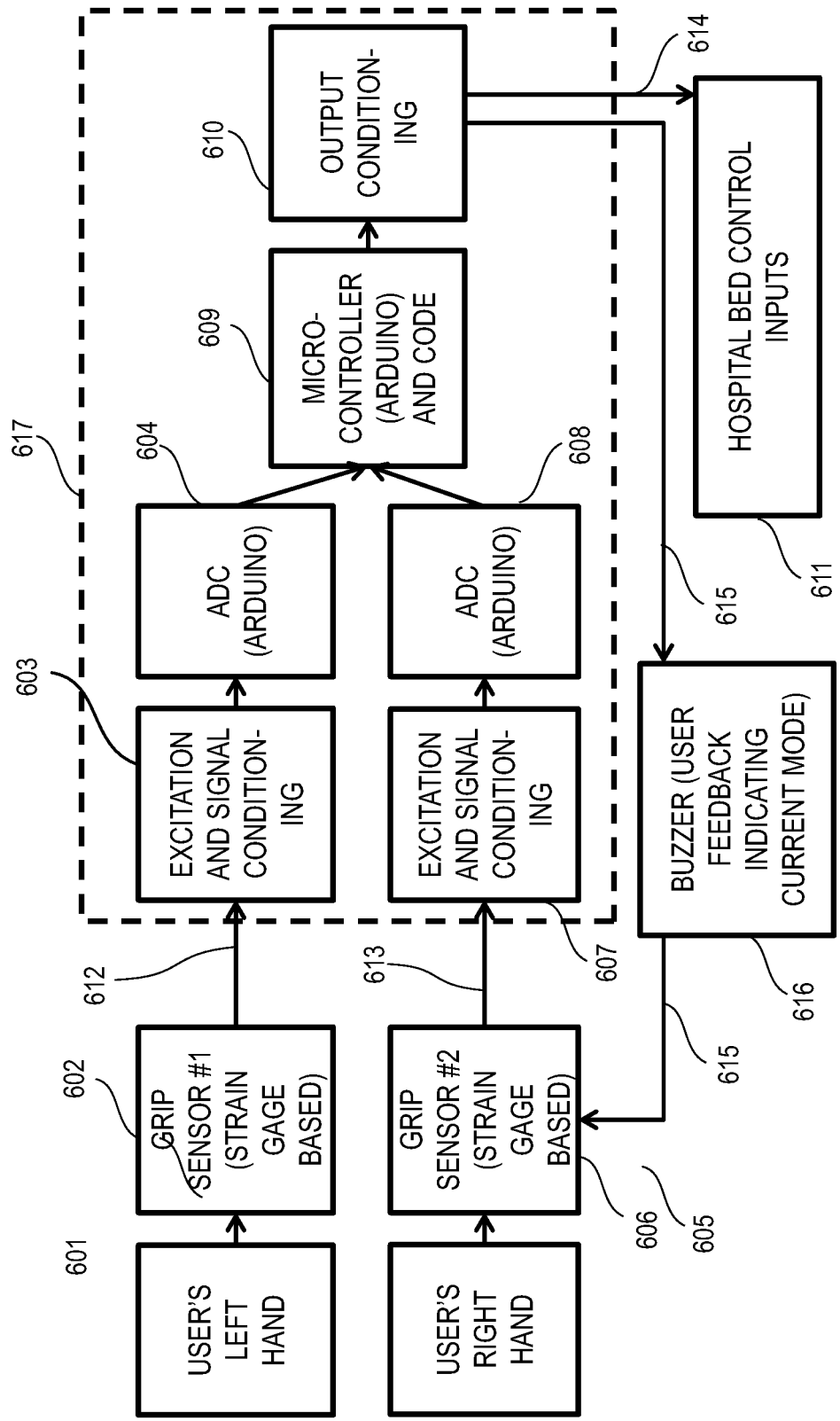
FIG. 6 is a block diagram of a specific embodiment of a two-pendant grip-sensing embodiment.

FIG. 6, the lead line, superimposed over the box 602 marked as "GRIP SENSOR #1 (STRAIN GAGE BASED)", should be moved upwards and to the left to connect reference numeral "601" to the box in the upper left of the page which is marked as "USER'S LEFT HAND"; the reference numeral "605" and associated lead line should be moved upwards and to the left to be associated with the box in the lower left of the page which is marked as "USER'S RIGHT HAND".

Figure 8:
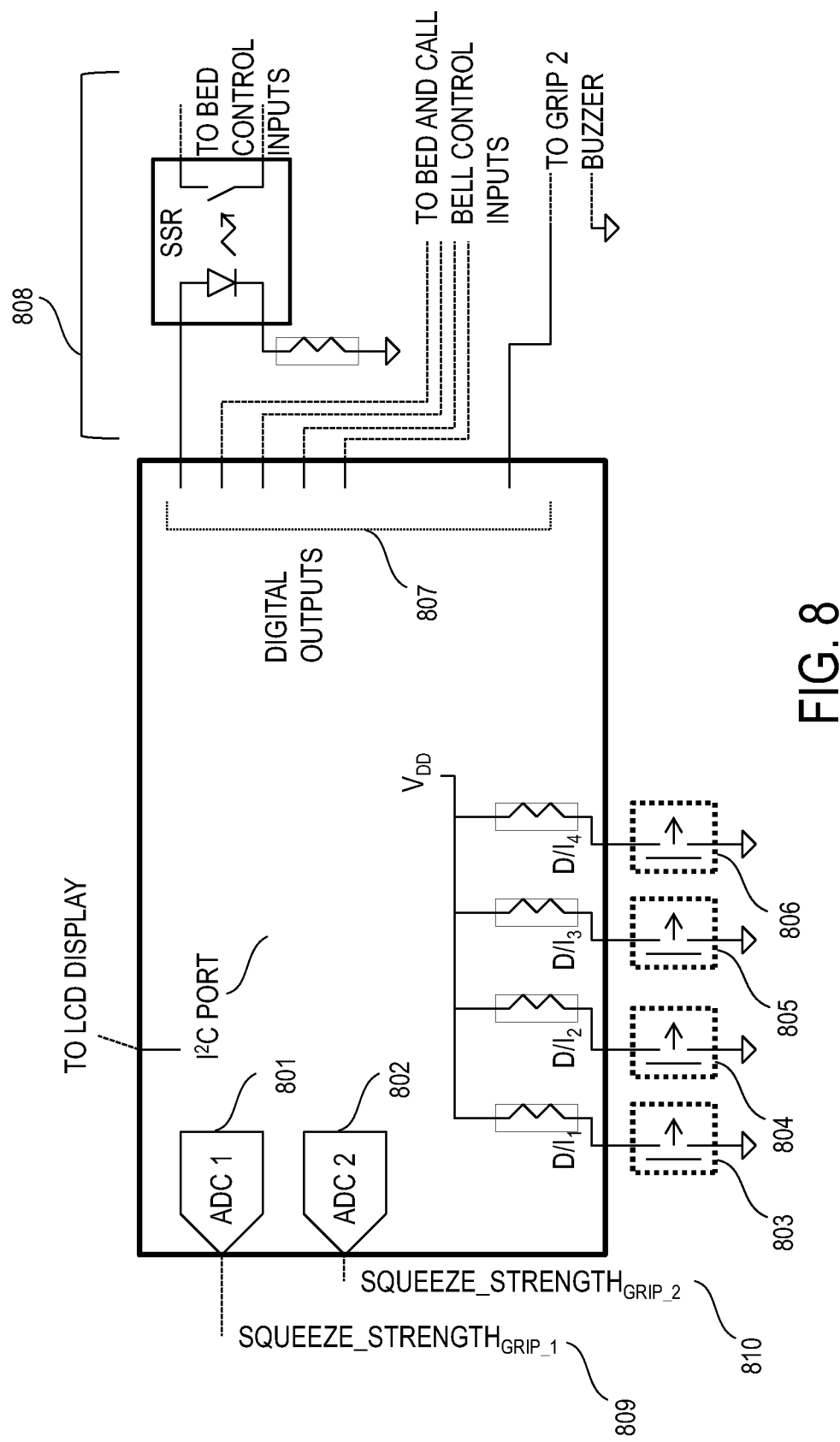
FIG. 8 is a schematic of the microcontroller comprising the decision making apparatus in a grip-sensing embodiment.

FIG. 8, the lead line pointing to the element denoted by the text "I2C PORT" should have reference numeral --811-- added and positioned beneath it such that the reference numeral "811" is associated with the element denoted by the text "I2C PORT".

Column 16, Lines 56 and 58, two references to "top housing shell 301", each occurrence, should read --top housing shell 302--; Lines 56-57 and 58-59, two references to "bottom housing shell 302", each occurrence, should read --bottom housing shell 306--.

Column 17, Line 27, "strain gage-based grip unit 603" should read --strain gage-based grip unit 606--; Lines 28-29, "components 603-610" should read --components 603-604 and 607-610--.

Column 18, Line 53, "1kOhm resister 905" should read --1kOhm resistor 907--.

Table 9, "Decision-making apparatus" etc row, in "Particular Embodiment of Element or Feature" Column 31:

1) "Potentiometer - TC33X-2-104E from Bourns" should be on its own line under "Instrumentation Amplifier - INA826AID from Texas Instruments;
2) the section headed by "cRIO EMBODIMENT" should be delineated more clearly from the section titled "ARDUINO EMBODIMENT", at least by a line break and/or line;
3) "FPGA backplane - NI cR10-9113" should read --FPGA backplane - NI cRIO-9113--;
4) "Real Time Controller - NI cR10-9024" should read --Real Time Controller - NI cRIO-9024--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*